United States Patent
Chang et al.

(10) Patent No.: US 11,285,121 B2
(45) Date of Patent: Mar. 29, 2022

(54) CALCIUM LACTATE COMPOSITIONS AND METHODS OF USE

(71) Applicant: MetiMedi Pharmaceuticals Co., Ltd., Incheon (KR)

(72) Inventors: Chong Hwan Chang, Incheon (KR); Keun-Yeong Jeong, Seoul (KR)

(73) Assignee: MetiMedi Pharmaceuticals Co., Ltd., Incheon (KR)

( * ) Notice: Subject to any disclaimer, the term of this patent is extended or adjusted under 35 U.S.C. 154(b) by 0 days.

(21) Appl. No.: 16/464,924

(22) PCT Filed: Jul. 7, 2017

(86) PCT No.: PCT/IB2017/054091
§ 371 (c)(1),
(2) Date: May 29, 2019

(87) PCT Pub. No.: WO2018/100442
PCT Pub. Date: Jun. 7, 2018

(65) Prior Publication Data
US 2019/0307712 A1 Oct. 10, 2019

(30) Foreign Application Priority Data

Nov. 30, 2016 (KR) .................. 10-2016-0161931

(51) Int. Cl.
| | | |
|---|---|---|
| *A61K 31/19* | (2006.01) | |
| *A23L 33/10* | (2016.01) | |
| *A61P 35/00* | (2006.01) | |
| *A61K 9/00* | (2006.01) | |
| *A61K 47/36* | (2006.01) | |
| *A61K 9/28* | (2006.01) | |
| *A61K 33/06* | (2006.01) | |
| *A23L 33/165* | (2016.01) | |
| *A61K 9/20* | (2006.01) | |
| *A61K 45/06* | (2006.01) | |
| *A61K 47/32* | (2006.01) | |
| *A61K 47/40* | (2006.01) | |
| *A61K 9/08* | (2006.01) | |
| *A61K 9/10* | (2006.01) | |
| *A61K 9/50* | (2006.01) | |
| *A61K 47/10* | (2017.01) | |
| *A61K 47/44* | (2017.01) | |

(52) U.S. Cl.
CPC .............. *A61K 31/19* (2013.01); *A23L 33/10* (2016.08); *A23L 33/165* (2016.08); *A61K 9/0019* (2013.01); *A61K 9/0024* (2013.01); *A61K 9/0053* (2013.01); *A61K 9/0056* (2013.01); *A61K 9/08* (2013.01); *A61K 9/10* (2013.01); *A61K 9/2054* (2013.01); *A61K 9/2081* (2013.01); *A61K 9/284* (2013.01); *A61K 9/2846* (2013.01); *A61K 9/2866* (2013.01); *A61K 9/5026* (2013.01); *A61K 9/5042* (2013.01); *A61K 33/06* (2013.01); *A61K 45/06* (2013.01); *A61K 47/10* (2013.01); *A61K 47/32* (2013.01); *A61K 47/36* (2013.01); *A61K 47/40* (2013.01); *A61K 47/44* (2013.01); *A61P 35/00* (2018.01); *A23V 2002/00* (2013.01); *A23V 2200/308* (2013.01); *A23V 2250/042* (2013.01); *A23V 2250/1578* (2013.01)

(58) Field of Classification Search
CPC ........ A61K 31/19; A61K 33/06; A61K 47/10; A61K 47/32; A61K 47/36; A61K 47/40; A61K 47/44; A61K 9/0019; A61K 9/0024; A61K 9/0056; A61K 9/08; A61K 9/10; A61K 9/2054; A61K 9/2081; A61K 9/284; A61K 9/2846; A61K 9/2866; A61K 9/5026; A61K 9/5042; A23V 2250/042; A23V 2250/1578; A23V 2002/00; A23V 2200/308; A23L 33/10; A23L 33/165; A61P 35/00; A61P 35/04; A61P 3/02; A61P 43/00
See application file for complete search history.

(56) References Cited

U.S. PATENT DOCUMENTS

| | | | | |
|---|---|---|---|---|
| 5,980,951 A | * | 11/1999 | Gardner | .............. A61K 31/551 424/464 |
| 2006/0115538 A1 | | 6/2006 | Krauskopf et al. | |
| 2012/0083531 A1 | | 4/2012 | Clarke et al. | |

FOREIGN PATENT DOCUMENTS

| | | | | | |
|---|---|---|---|---|---|
| CN | 102823872 A | * | 12/2012 | | |
| EP | 2599477 A1 | | 6/2013 | | |
| KR | 1020140037278 A | | 3/2014 | | |
| WO | WO-2014145219 A1 | * | 9/2014 | ............. | A61K 33/10 |
| WO | WO-2015177329 A1 | * | 11/2015 | ........... | G01N 33/502 |
| WO | 2016108446 A1 | | 7/2016 | | |

OTHER PUBLICATIONS

Kim et. al., WO 2016108446, publ Jul. 7, 2016, English translation, pp. 1-95 (Year: 2016).*

Jang et. al., Life Sciences, publ Aug. 24, 2015, Elsevier, vol. 139, pp. 160-165 (Year: 2015).*

(Continued)

*Primary Examiner* — Sarah Pihonak
(74) *Attorney, Agent, or Firm* — Arent Fox LLP

(57) ABSTRACT

The invention relates to pharmaceutical compositions comprising calcium lactate as an active agent and a polysaccharide, polymer, lipid, or a combination thereof. The pharmaceutical compositions are useful treating cancer. The invention also relates to foods and nutrient compositions comprising calcium lactate.

19 Claims, 12 Drawing Sheets

(56) References Cited

OTHER PUBLICATIONS

Yang et. al., CN 102823872A, publ. Dec. 19, 2012, English translation, pp. 1-8 (Year: 2012).*
NCI, "What is Cancer?", publ. Feb. 9, 2015, NIH, pp. 1-16 (Year: 2015).*
Bhatia et. al., Nature Biotechnology, 2012, NPG, vol. 30(7), pp. 604-610 (Year: 2012).*
Leaf, Fortune, 2004, Time Inc., pp. 1-26 (Year: 2004).*
Kaiser, Science, AAAS, vol. 337, pp. 282-284 (Year: 2012).*
Wistuba et. al., Nature Reviews Clinical Oncology, 2011, NPG, vol. 8, pp. 135-141 (Year: 2011).*

* cited by examiner

CALCIUM LACTATE COMPOSITIONS AND METHODS OF USE

CROSS-REFERENCE TO RELATED APPLICATIONS

This application claims priority to KR 10-2016-0161931 filed Nov. 30, 2016, which is herein incorporate by reference in its entirety.

BACKGROUND OF THE INVENTION

Field of the Invention

The invention relates to pharmaceutical compositions comprising calcium lactate and methods of use for treating cancer or suppressing metastasis. The pharmaceutical compositions can comprise, for example, polysaccharides, polymers, lipids, and/or combinations thereof. The invention also relates to foods and nutrient compositions comprising calcium lactate.

Background

Calcium lactate has excellent bioavailability and body absorption and has not been known as having a side effect and thus has been used mainly as a calcium enhancer or a pH regulator of foods. However, it has been discovered that calcium lactate is useful as an active agent for treating cancer and suppressing metastasis. See WO2016/108446, which is herein incorporated by reference in its entirety. Administration of calcium lactate to cancer cells showed that: the levels of lactate, LDH-B (lactate dehydrogenase B), which affects metabolism of lactate, pyruvate, PDH (pyruvate dehydrogenase), which affects metabolism of pyruvate, and α-KG (α-ketoglutarate) in cells are increased; the levels of β-catenin, as a cancer growth factor, PARP, which suppresses intracellular DNA damage, HIF-1α (hypoxia inducible factor 1α) and VEGF (vascular endothelial growth factor), which affect cancer cell metastasis, invasion, and angiogenesis in cells are decreased; and the levels of growth, metastasis (migration), and tube formation of the cancer cells are decreased. See WO2016/108446.

Further, the anticancer activity of calcium lactate was measured using animal models, which showed that administration of calcium lactate suppressed growth of cancer cells in animal models. See WO2016/108446.

Administration of calcium lactate in combination with conventional radiation showed that an equivalent anticancer effect can be obtained with a decreased amount of radiation as compared with the conventional amount of radiation. See WO2016/108446. Also, administration to relevant cancer cell lines of calcium lactate in combination with various kinds of well-known anticancer drugs showed that a higher anticancer effect can be obtained with a decreased concentration of the anticancer drugs as compared with administration of the well-known anticancer drugs alone. See WO2016/108446.

Novel pharmaceutical and nutrient compositions and foods containing calcium lactate are needed for treatment of cancer or reducing the risk of cancer.

SUMMARY OF THE INVENTION

The invention is directed to pharmaceutical compositions comprising a therapeutically effective amount of calcium lactate as an active agent for treating cancer and a pharmaceutically acceptable polysaccharide, polymer, lipid, or combinations thereof. In some embodiments, the composition comprises the calcium lactate and the polysaccharide. In some embodiments, the weight ratio of the calcium lactate and the polysaccharide is 1:<0.2 to 1:5, 1:<0.2, or 1:0.2 to 1:5.

In some embodiments, the composition further comprises a polymer and/or lipid. In some embodiments, the weight ratio of the polymer and lipid is 1:0.1 to 1:50, at least 1:5, or 1:5 to 1:30.

In some embodiments, the composition comprises calcium lactate and the polymer and/or lipid. In some embodiments, the weight ratio of the polymer and lipid is 1:0.1 to 1:50, at least 1:5, or 1:5 to 1:30.

In some embodiments, the composition is short-acting or long-acting. The composition can be, e.g., an injectable composition.

In some embodiments, the polysaccharide can be a cellulose derivative, pectin, hyaluronic acid, starch, guar gum, chitosan, gelatin, collagen, alginate, alginic acid or combinations thereof. In some embodiments, the polymer can be a poloxamer series, polyvinylpyrrolidone, polyethylene glycol (PEG), polyglycolic lactic acid (PLGA) series, or combinations thereof. In some embodiments, the lipid can be a mono- or tri-fatty acid glycerin ester or polyethylene glycol complexes thereof, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

In some embodiments, upon placement of the composition in an in vitro dissolution test comprising an elution test method at 300 rpm in 200 ml having a pH of 6.8 at 37° C. using a nylon filter having a pore size of 45 μm, at least about 40% of the active agent is released after 6 hours, at least about 60% of the active agent is released after 12 hours, at least about 80% of the active agent is released after 24 hours, and/or at least about 90% of the active agent is released after 48 hours.

In some embodiments, upon placement of the composition in an in vitro dissolution test comprising an elution test method at 300 rpm in 200 ml having a pH of 6.8 at 37° C. using a nylon filter having a pore size of 45 μm, less than about 40% of the active agent is released after 24 hours, less than about 60% of the active agent is released after 48 hours, less than about 80% of the active agent is released after 72 hours, and/or less than about 90% of the active agent is released after 144 hours.

The invention is also directed to a sterile glass or polyolefin container comprising the compositions described herein.

The invention is also directed to pharmaceutical compositions comprising a therapeutically effective amount of calcium lactate as an active agent for treating cancer, wherein the calcium lactate is coated with a pharmaceutically acceptable enteric coating.

In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments, the weight ratio of the calcium lactate and the enteric coating is 10:0.5 to 1:1.5.

In some embodiments, in an in vitro dissolution test comprising a USP Paddle method at a paddle speed of 50 rpm at 37° C., when the composition described herein is placed in 0.1 N HCl for 120 minutes followed by adjusting to pH 6.8 with phosphate buffer for 60 minutes, less than about 20% of the active agent is released after 30 minutes, less than 30% of the active agent is released after 60 minutes, less than 50% of the active agent is released after 120 minutes, and/or less than 10% of the active agent is released after 120 minutes.

The invention is also directed to methods of treating cancer in a subject in need thereof, comprising administer the compositions described herein. In some embodiments, the cancer is lung cancer, breast cancer, colorectal cancer, stomach cancer, brain cancer, pancreatic cancer, thyroid cancer, skin cancer, bone cancer, lymphoma, uterine cancer, cervical cancer, kidney cancer, or melanoma. In some embodiments, a second anticancer agent can be administered. In some embodiments, the second anticancer agent is Imatinib, 5-FU (5-Florouracil), Irinotecan, Sunitinib, Oxaliplatin, Paclitaxel, Lapatinib, Trastuzumab (Herceptin), Gefitinib, Erlotinib, Methotrexate, Carboplatin, Docetaxel, Everolimus, Sorafenib, a carbonic anhydrase inhibitor, and a monocarboxylate transporter inhibitor. In some embodiments, the calcium lactate and the second anticancer agent are administered simultaneously or sequentially.

In some embodiments, the methods further comprise administering radiation. The radiation is provided to the subject in an amount of, e.g., 2 Gy to 10 Gy per day.

The invention is also directed to food or nutrient compositions comprising an effective amount of calcium lactate to reduce the risk of cancer, such as, e.g., an injectable nutritional supplement.

DETAILED DESCRIPTION OF THE INVENTION

Pharmaceutical Compositions

Figure 1:
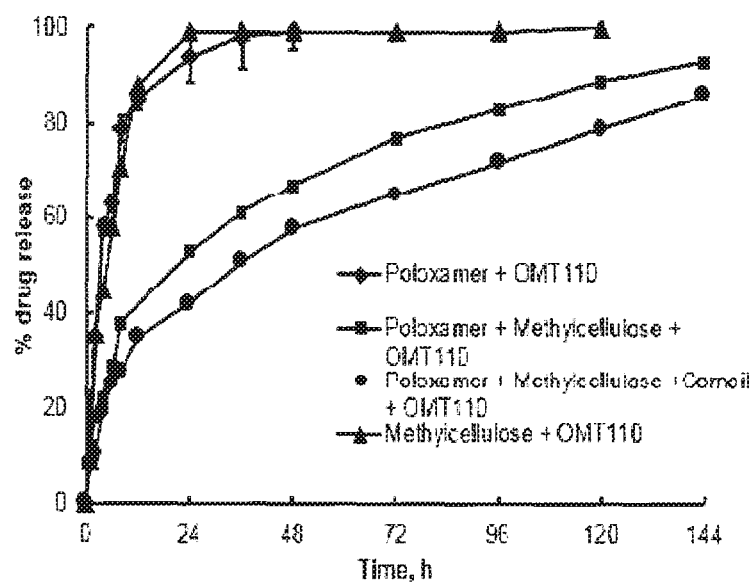
FIGS. 1 and 2. Drug release results of some exemplary formulations of the invention.

The term "calcium lactate" refers to a type of lactate metal salt that can, for example, exist as a hydrate, represented by $C_6H_{10}O_6Ca.5H_2O$ in which calcium ion is bonded to lactate. Calcium lactate can be in the form of white powder or granules at room temperature, anhydrous at a 120° C. heating condition, and has a solubility of 5% (w/v).

Calcium lactate can be formulated into pharmaceutical compositions for treating cancer. Because calcium bound to lactate is more absorbable into cancer cells than normal cells, calcium lactate has the advantage of relatively higher efficiency of lactate delivery to cancer cells than other types of lactate metal salts.

In various embodiments, the invention provides a pharmaceutical composition comprising a therapeutically effective amount of calcium lactate as an active agent for treating cancer and a pharmaceutically acceptable polysaccharide, polymer, lipid, or combinations thereof. In some embodiments, the pharmaceutical composition comprises the calcium lactate and the polysaccharide.

In some embodiments, the invention provides an enteric coating of the calcium lactate such that the active agent is protected from the acidic environment of the stomach and absorbed in the small intestine before it reaches the large intestine when the active agent is administered orally.

The present invention also provides short-acting and long-acting pharmaceutical compositions comprising calcium lactate. In some embodiments, the long-acting compositions comprise calcium lactated coated with at least one enteric-coating material such as hydroxypropyl methyl cellulose phthalate (HPMCP), cellulose acetate phthalate (CAP), polyvinyl acetate phthalate (PVAP), shellac and a polymer of methacrylic acid, and an ester thereof.

The pharmaceutical composition of the invention can be formulated into pharmaceutical preparations for oral administration. Examples of the preparation include powders, tablets, capsules, granules or syrups, tablets and capsules, but not limited thereto.

The present inventors developed formulations of hydrogels particularly methylcellulose, poloxamer, pectin, and alginate hydrogel which can remain in a solution or nanoparticle form in vitro, and the gel can form when injected into the body and allow sustained release of calcium lactate. The relatively short drug release time which is the weakness of the hydrogel has been improved by increasing the interaction between the drug and hydrogel or by delaying the diffusion of the drug in the hydrogel.

The weight ratio of the calcium lactate and the polysaccharide can be, e.g., 1:<0.2 to 1:5, 1:0.01 to 1:5, 1:0.05 to 1:5, or 1:0.1 to 1:5. The weight ratio of the calcium lactate and the polysaccharide can be 1:<0.2. The weight ratio of the calcium lactate and the polysaccharide can be 1:0.2 to 1:5.

In some embodiments, the pharmaceutical composition further comprises a polymer or lipid. The weight ratio of the calcium lactate and the polymer or lipid can be at least 1:5. The weight ratio of the calcium lactate and the polymer or lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition further comprises a polymer and lipid. The weight ratio of the calcium lactate and the polymer and lipid can be at least 1:5. The weight ratio of the calcium lactate and the polymer and lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition comprises the calcium lactate and the polymer or lipid. The weight ratio of the calcium lactate and the polymer or lipid can be at least 1:5. The weight ratio of the calcium lactate and the polymer or lipid can be 1:5 to 1:30. The weight ratio of the calcium lactate and the polymer or lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition comprises the calcium lactate and the polymer and lipid. The weight ratio of the calcium lactate and the polymer and lipid can be at least 1:5. The weight ratio of the calcium lactate and the polymer and lipid can be 1:5 to 1:30. The weight ratio of the calcium lactate and the polymer and lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the weight ratio of the polymer and the lipid can be 1:0.1 to 1:50, 1:0.1 to 1:20, 1:0.1 to 1:10, 1:0.1 to 1:5, 1:0.1 to 1:2, 1:0.1 to 1:1, 1:0.1 to 0.5, or 1:0.1 to 1:0.2.

Polysaccharides suitable for use in the composition can be a cellulose derivative (e.g., carboxymethyl cellulose (CMC), ethyl cellulose (EC), hydroxypropyl methyl cellulose (HPMC), methyl cellulose (MC)), pectin, hyaluronic acid, starch, guar gum, chitosan, gelatin, collagen, alginate, alginic acid, or combinations thereof.

Polymers suitable for use in the composition can be a poloxamer series, polyvinylpyrrolidone, polyethylene glycol (PEG), polyglycolic lactic acid (PLGA) series, or combinations thereof.

Lipids suitable for use in the composition can be a mono- or tri-fatty acid glycerin ester or polyethylene glycol complexes thereof, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

The invention is further directed to a pharmaceutical composition comprising a therapeutically effective amount of calcium lactate as an active agent for treating cancer, wherein the calcium lactate is coated with a pharmaceutically acceptable enteric coating. In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments, the weight ratio of the calcium lactate and the enteric coating is 10:0.5 to 10:15, 10:0.5 to 1:1, 10:0.5 to 10:5, 10:0.5 to 10:3, 10:0.5 to 10:2, 10:0.5 to 10:1, 10:0.5 to 1:0.8.

By "pharmaceutically acceptable," as used herein, refers a material, such as a carrier or diluent, which does not abrogate the biological activity or properties of the compound, and is relatively nontoxic, i.e., the material can be administered to an individual without causing undesirable biological effects or interacting in a deleterious manner with any of the components of the composition in which it is contained.

A pharmaceutical composition, as used herein, refers to a mixture of calcium lactate with other chemical components that are pharmaceutically acceptable, such as but not limited to carriers, stabilizers, diluents, disintegrants, suspending agents, thickening agents, binders, antimicrobial agents, antimicrobial preservatives, antioxidants, and/or buffering agents. The pharmaceutical composition facilitates administration of the calcium lactate to a subject.

The term "carrier," as used herein, refers to relatively nontoxic chemical compounds or agents that facilitate the incorporation of a compound into cells or tissues. The term "diluent" refers to chemical compounds that are used to dilute the compound of interest prior to delivery. Diluents can also be used to stabilize compounds because they can provide a more stable environment. Pharmaceutically acceptable additives include diluents, binders, solubilizers, solubility enhancers, pore formers, osmotic agents, gas formers, lubricants and fluidizers well known in the art, but not limited thereto.

Diluents can include lactose, fructose, dextrose, sucrose, maltose, microcrystalline cellulose, starch, calcium hydrogen phosphate, mannitol or a mixture thereof, but not limited thereto. ther diluents include microcrystalline cellulose, lactose, mannitol, calcium phosphate and the like.

Examples of binders can include povidone, hydroxypropylcellulose, polyvinylalcohol, hydroxypropylmethylcellulose, carboxymethyl-cellulose sodium and thereof.

Solubilizing agents include surfactants, cyclodextrins and derivatives thereof, lipophilic substances or mixtures thereof, but are not limited thereto.

Surfactants include water soluble or water dispersible nonionic, nonpolar nonionic, anionic, cationic, amphoteric or ionic surface activators or mixtures thereof, but are not limited thereto.

Examples of disintergrants include crospovidone, croscarmellose sodium, glycolic acid starch sodium, and examples of the lubricant include magnesium stearate, calcium stearate, sodium stearyl fumarate and thereof.

The pharmaceutical compositions of the invention can further include antimicrobial agents, such as benzyl alcohol, chlorobutanol, phenylethyl alcohol, phenyl-mercuric acetate, potassium sorbate, and sorbic acid. Antifungal agents include such compounds as benzoic acid, butylparaben, ethylparaben, methylparaben, propylparaben, and sodium benzoate.

Antimicrobial preservatives can be added to the pharmaceutical compositions of the present invention in order to protect them against the growth of potentially harmful microorganisms, which usually invade the aqueous phase, but in some cases can also grow in the oil phase of a composition. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, and trisodium ethylenediamine tetracetate (EDTA).

Antioxidants can be added to protect all of the ingredients of the pharmaceutical compositions from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyloctyl and dodecyl gallate, sodium metabisulfite, sulfur dioxide, and tocopherols.

Buffering agents can be used to maintain a desired pH of the pharmaceutical compositions once established, from the effects of outside agents and shifting equilibria of components of the composition.

The pharmaceutical compositions described herein can be prepared following techniques known in the art, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

In some embodiments, the pharmaceutical compositions of the invention are short-acting. The term "short-acting" refers to a composition that releases substantially all of the active agent within 48 hours when tested in an in vitro dissolution test described herein, for example, from time of delivery, time 0, until about 1 hour to about 48 hours, until about 3 hours to about 24 hours, until about 6 hours to about 24 hours, or until about 12 hours to about 24 hours.

For example, upon placement of the composition in an in vitro dissolution test comprising an elution test method (e.g., from Labfine Co., Mumbai, India) at 300 rpm in 200 ml having a pH of 6.8 at 37° C. using a nylon filter having a pore size of 45 μm, at least about 40% of the active agent is released after 6 hours, at least about 60% of the active agent is released after 12 hours, at least about 80% of the active agent is released after 24 hours, and/or at least about 90% of the active agent is released after 48 hours. In some embodiments, upon placement of the composition in an in vitro dissolution test comprising an elution test method (e.g., from Labfine Co., Mumbai, India) at 300 rpm in 200 ml having a pH of 6.8 at 37° C. using a nylon filter having a pore size of 45 μm, at least about 40% to about 60% of the active agent is released after 6 hours, at least about 60% to about 80% of the active agent is released after 12 hours, at least about 80% to about 90% of the active agent is released after 24 hours, and/or at least about 90% to about 100% of the active agent is released after 48 hours.

In some embodiments, the pharmaceutical compositions of the invention are long-acting. The term "long-acting" is intended to mean composition that releases the active agent slowly after the initial dosage, for example, from time of delivery, time 0, until about 48 hours to about 192 hours, until about 72 hours to about 192 hours, until about 96 hours to about 192 hours, until about 120 hours to about 192 hours, or until about 144 hours to about 192 hours.

In some embodiments, upon placement of the composition in an in vitro dissolution test comprising an elution test method (e.g., from Labfine Co., Mumbai, India) at 300 rpm in 200 ml having a pH of 6.8 at 37° C. using a nylon filter having a pore size of 45 μm, less than about 40% of the active agent is released after 24 hours, less than about 60% of the active agent is released after 48 hours, less than about 80% of the active agent is released after 72 hours, less than about 90% of the active agent is released after 144 hours. In some embodiments, upon placement of the composition in an in vitro dissolution test comprising an elution test method (e.g., from Labfine Co., Mumbai, India) at 300 rpm in 200 ml having a pH of 6.8 at 37° C. using a nylon filter having a pore size of 45 μm, about 20% to about 50% of the active agent is released after 24 hours, about 20% to about 40% of the active agent is released after 24 hours, about 40% to about 70% of the active agent is released after 48 hours, about 40% to about 60% of the active agent is released after 48 hours, about 40% to about 80% of the active agent is released after 72 hours, about 50% to about 80% of the active agent is released after 72 hours, about 60% to about 90% of the active agent is released after 144 hours, or about 70% to about 90% of the active agent is released after 144 hours.

In some embodiments, upon placement of the composition in an in vitro dissolution test comprising a USP Paddle method at a paddle speed of 50 rpm at 37° C., when the composition is placed in 0.1 N HCl for 120 minutes followed by adjusting to pH 6.8 with phosphate buffer for 60 minutes, less than about 20% of the active agent is released after 30 minutes, less than 30% of the active agent is released after 60 minutes, less than 50% of the active agent is released after 120 minutes, and/or less than 10% of the active agent is released after 120 minutes.

In some embodiments, the pharmaceutical compositions of the invention are injectable dosage forms. For parenteral injections, appropriate formulations can include aqueous or nonaqueous solutions, preferably with physiologically compatible carriers.

Pharmaceutical formulations for parenteral administration include aqueous solutions of the active compound(s) in water-soluble form. Additionally, suspensions of the active agent can be prepared as appropriate oily injection suspensions. Suitable lipids or lipophilic carriers include fatty oils such as sesame oil, or synthetic fatty acid esters, such as ethyl oleate or triglycerides, or liposomes. The lipid can be a mono- or tri-fatty acid glycerin ester or polyethylene glycol complexes thereof, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

Since the medical application of hydrogels, numerous hydrogels have been developed and studied in many fields, including the medical, pharmaceutical, and cosmetic industries. Although hydrogels are generally biocompatible, they have various problems that are limiting the delivery of a drug, and various efforts are made to solve the problems. A hydrogel is a three-dimensional structure composed of a network of hydrophilic polymers. More than 90% of the components are composed of water. Hydrogels have been actively studied in the biomedical field due to their similarity to bio-tissue such as high moisture content, porous structure, relatively soft properties, and biocompatibility. Hydrogels can exhibit various properties depending on the kind of polymer used as the main chain or the crosslinking method adopted. When a polymer of polyacrylic acid series polymer or a synthetic compound such as polyvinyl alcohol is used, the biocompatibility is low, but the chemical modification is easy, so that the engineering application is very easy. On the other hand, when natural compounds, especially pectin, alginate, collagen, fibrin and hyaluronic are used as the main chain, the chemical modification is difficult. Nevertheless, there are advantages of using these materials that are biologically derived components, as it is suitable for clinical application and there are few side effects such as immune inflammation reaction at the time of transplantation.

It is the cross linking method that affects the properties of the hydrogel as well as the type of polymer used. Even if the same polymer is used as the main chain, the hydrogel having completely different characteristics can be obtained if the crosslinking method is different. The method of crosslinking hydrogels can be broadly divided into physical and chemical methods. Physical crosslinking methods include ionic interaction, hydrophobic interaction, hydrogen bond, and reversible crosslinking by structural entanglement. These crosslinking methods can easily induce the formation of a three-dimensional network structure without the need for a separate chemical additive or complicated process. On the other hand, the chemical crosslinking method typically forms covalent bond that result an irreversible and stable network as compared with the physical crosslinking method. Hydrogels with excellent biocompatibility and various physicochemical properties have been extensively studied in biomedical fields such as drug delivery and tissue engineering. Most hydrogels exhibit shorter drug release time than other drug delivery systems due to their high water content, and there is a need to develop a system with a longer drug release time.

In some embodiments, the pharmaceutical compositions of the invention are oral dosage forms. For oral administration, the compound described herein can be formulated readily by combining the active agent with pharmaceutically acceptable carriers or excipients well known in the art. Such carriers enable the active agent described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid carriers with the compound described herein, optionally grinding the resulting mixture, and processing the mixture of granules, after adding suitable auxiliaries, if desired, to obtain tablets or dragee cores. Suitable excipients include, but are not limited to, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents can be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical compositions can be formulated in conventional manner using one or more pharmaceutically acceptable carriers comprising excipients and auxiliaries which facilitate processing of the active agent into preparations which can be used pharmaceutically. Proper formulation is dependent upon the route of administration chosen. Any of the well-known techniques can be used as suitable and as understood in the art. Pharmaceutical compositions described herein can be manufactured in a conventional manner, such as, by way of example only, by means of conventional mixing, dissolving, granulating, dragee-making, levigating, emulsifying, encapsulating, entrapping or compression processes.

Aqueous suspensions can also contain one or more polymers as suspending agents. The polymer can be a poloxamer series, polyvinylpyrrolidone, polyethylene glycol (PEG), polyglycolic lactic acid (PLGA) series, or combinations thereof. Other useful polymers include water-soluble polymers such as cellulosic polymers, e.g., hydroxypropyl methylcellulose, and water-insoluble polymers such as cross-linked carboxyl-containing polymers. Useful compositions can also include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran.

In some embodiments, provided are pharmaceutical dosage forms comprising calcium lactate and a pharmaceutically acceptable enteric coating in order to control the release of the active agent. In some embodiments, the coating is a film and, in another embodiment, it is a membrane. The enteric coating, e.g., film or membrane, can serve to delay release until after the stomach and to protect the active agent from gastric fluid. The enteric coating can comprise one or more substances preferably of a polymeric nature (e.g., methacrylates etc.; polysaccharides etc. as described in more detail below) or combination of more than one such substance, optionally including other excipients, such as, for example, plasticizers. In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments of the invention the composition comprises a hydrogel-forming polymer and further polymers able to achieve a desired delay (or other change) in the release of the active agent.

In the case of tablets for oral use, carriers which are commonly used include lactose and corn starch. Lubricating agents, such as magnesium stearate, are also typically added. For oral administration in a capsule form, useful diluents include lactose and dried corn starch.

The sterile injectable preparation can also be a sterile injectable suspension in a non-toxic parenterally acceptable carrier such as lipids.

The amount of calcium lactate included in the pharmaceutical compositions can be, but is not limited to, from 1 wt % to 50 wt %, from 1 wt % to 40 wt %, from 1 wt % to 35 wt %, from 1 wt % to 30 wt %, from 1 wt % to 20 wt %, from 1 wt % to 15 wt %, or from 1 wt % to 10 wt % based on the total weight of the final composition. The concentration of the calcium lactate included in a single dose of the pharmaceutical composition can be, but is not limited to, 2.5 mM to 100 mM, 2.5 mM to 50 mM, 2.5 mM to 25 mM, 5 mM to 100 mM, 5 mM to 50 mM, 5 mM to 25 mM, 10 mM to 100 mM, 10 mM to 50 mM, or 10 mM to 25 mM.

Solid oral pharmaceutical compositions can be prepared by conventional techniques such as dry granulation, direct compression, wet granulation, extrusion spheronization, melt granulation or compression coating, but not limited thereto. The coating can be applied as described below and can vary as to thickness and density. The amount of coating is defined by the additional weight added to (gained by) the dry composition (e.g., bead or core containing the calcium lactate) of the invention. Weight gain can be in the range of 0.1% to 50%, 1% to 20%, 1% to 15%, 3% to 10%, 5% to 12%, or 8% to 12%.

The coating process can be carried out by any suitable means such as, for example, by use of a coating machine which applies a solution of a polymer coat (as described above in particular) to the composition. Polymers for coating are either provided by the manufacturer in ready-made solutions for direct use or can be made up before use following manufacturers' instructions.

Unit Dosages and Kits

The term "unit dosage form" refers to a physically discrete unit suitable as a single dosage, each unit containing a predetermined quantity of active ingredient, in association with a suitable pharmaceutical excipient, by which one or more is used throughout the dosing regimen to produce a desired therapeutic effect, e.g., treating cancer and/or suppressing metastasis of cancer.

The pharmaceutical compositions described herein can be in unit dosage forms suitable for single administration of precise dosages. In unit dosage form, the formulation is divided into unit doses containing appropriate quantities of one or more active agents. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection can be presented in unit dosage form, which include, but are not limited to ampoules, or in multi-dose containers.

The daily dosages appropriate for calcium lactate can be from about 1 mg/kg to about 1000 mg/kg, about 10 mg/kg to about 750 mg/kg, about 10 mg/kg to about 500 mg/kg, or about 100 mg/kg to 500 mg/kg per body weight. An indicated daily dosage in the larger mammal, including, but not limited to, humans, is in the range from about 5 mg to about 100,000 mg, conveniently administered in divided doses, including, but not limited to, up to four times a day or in long-acting form. Suitable unit dosage forms for administration include from about 10 mg to about 1000 mg, about 100 mg to about 1000 mg, about 500 mg to about 750 mg, about 25 mg to about 250 mg, about 50 mg to about 100 mg, about 10 mg to about 200 mg, or about 10 mg to about 250 mg of the active agent. The administration frequency of the composition of the present disclosure can be, but is not particularly limited to, once, twice, three times, four times, etc. divided doses a day. An appropriate "effective" amount in any individual case can be determined using techniques, such as a dose escalation study.

The foregoing ranges are merely suggestive, as the number of variables in regard to an individual treatment regime is large, and considerable excursions from these recommended values are not uncommon. Such dosages can be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of the active agent lies preferably within a range of circulating concentrations that include the $ED_{50}$ with minimal toxicity. The dosage can vary within this range depending upon the dosage form employed and the route of administration utilized.

According to the present invention, the pharmaceutical compositions can be in the form of a sterile injectable preparation, for example a sterile injectable aqueous or oleaginous suspension. The pharmaceutical compositions of the present invention can be orally administered in any orally acceptable dosage form including, but not limited to, capsules, tablets, aqueous suspensions or solutions.

The invention is also directed to a sterile glass or polyolefin container comprising a pharmaceutical composition disclosed herein. In some embodiments, the container is non-DEHP (Bis(2-ethylhexyl) phthalate (di-2-ethylhexyl phthalate, diethylhexyl phthalate, DEHP; dioctyl phthalate, DOP) or non-PVP (Polyvinylpyrrolidone).

A kit comprises suitable containers, such as boxes, individual bottles, bags or ampoules. Suspension compositions can be packaged in single-dose non-reclosable containers or multiple-dose reclosable containers.

Methods of Treatment and Cancers

The invention is also directed to methods of treating cancer in a subject in need thereof, comprising administering a pharmaceutical composition described herein, comprising a therapeutically effective amount of calcium lactate as an active agent for treating cancer.

The term "cancer" as used herein refers to an abnormal growth of cells, which tend to proliferate in an uncontrolled way and, in some cases, to metastasize (spread). The types of cancer suitable for treatment by the methods described herein include, but are not limited to, lung cancer, breast cancer, colorectal cancer, stomach cancer, brain cancer, pancreatic cancer, thyroid cancer, skin cancer, bone cancer, lymphoma, uterine cancer, cervical cancer, kidney cancer, and melanoma. In some embodiments, the cancer is a metastatic cancer such as, but not limited to, lung cancer, breast cancer, colorectal cancer, stomach cancer, brain cancer, pancreatic cancer, thyroid cancer, skin cancer, bone cancer, lymphoma, uterine cancer, cervical cancer, kidney cancer, and melanoma. Cancers which can be treated with the pharmaceutical compositions provided in the present disclosure are not particularly limited as long as growth, invasion, and metastasis thereof can be suppressed or decreased, for example, by disturbing metabolism thereof.

The term "subject" or "patient" encompasses mammals and non-mammals. Examples of mammals include, but are not limited to, any member of the mammalian class: humans, nonhuman primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human or a nonhuman.

As used herein, "treat", "treating", or "treatment" of cancer by administration of the pharmaceutical composition refers to any lessening of severity, delay in onset, slowing of progression, or shortening of duration of cancer or metastasis of cancer, whether permanent or temporary, lasting or transient that can be attributed to or associated with administration of the composition.

In some embodiments, the methods further comprise administering a second anticancer agent. The second anticancer agent can include Imatinib, 5-FU (5-Florouracil), Irinotecan, Sunitinib, Oxaliplatin, Paclitaxel, Lapatinib, Trastuzumab (Herceptin), Gefitinib, Erlotinib, Methotrexate, Carboplatin, Docetaxel, Everolimus, Sorafenib, a carbonic anhydrase inhibitor, and a monocarboxylate transporter inhibitor.

In some embodiments, the calcium lactate and the second anticancer agent are administered simultaneously. In some embodiments, the calcium lactate and the second anticancer agent are administered sequentially.

Calcium lactate shows improved anticancer activity in cases of administration in combination with a publicly known anticancer drug. This is because the publicly known anticancer drug may not have a mechanism involved in glycolysis of a cancer cell. Therefore, co-administration of the active agent, calcium lactate, and a publicly-known anticancer drug can be used more effectively for treating cancer. However, in some embodiments, calcium lactate is the only active agent used in the methods or compositions described herein.

The active agent, calcium lactate, can suppress various characteristics which can induce metastasis of cancer cells, such as metastasis, invasion, angiogenesis of cancer cells, tube formation, cell migration, colony-forming ability, etc., and, thus, can be used as an active ingredient of a pharmaceutical composition for suppressing cancer metastasis.

A metastasis-suppressed target cancer is the same as defined above. For example, the pharmaceutical composition for suppressing cancer metastasis can be used for suppressing the occurrence of one or more metastatic cancers such as metastatic lung cancer, breast cancer, colorectal cancer, stomach cancer, brain cancer, pancreatic cancer, thyroid cancer, skin cancer, bone cancer, lymphoma, uterine cancer, cervical cancer, kidney cancer, and melanoma.

The methods of the invention can further comprise administering radiation. The radiation can be provided to the subject in an amount of 2 Gy to 10 Gy per day. Thus, in case of administration of the composition in combination with radiation, the metal lactate salts improve the anticancer activity of radiation. Therefore, it is possible to obtain an equivalent anticancer effect with a decreased amount of radiation as compared with the conventional case. In this case, the amount of radiation is not particularly limited, and can be 2 to 10 Gy per day. The radiation can be irradiated once per day, or can be irradiated over several days by dividing the amount of radiation.

The term "co-administration" or the like, as used herein, is meant to encompass administration of the selected two or more active agents to a single patient, and is intended to include treatment regimens in which the agents are administered by the same or different route of administration or at the same or different time.

The pharmaceutical composition of the present disclosure can be administered in a therapeutically effective amount, and as used herein, the term "effective amount" or therapeutically effective amount" refers to an amount sufficient to treat or prevent diseases, at a reasonable benefit/risk ratio applicable to any medical treatment or prevention. The effective dosage level can be determined depending on severity of the disease, activity of the drug, a patient's age, body weight, health and sex, sensitivity to the drug, administration time, administration route, and excretion rate of the composition of the present disclosure, duration of treatment, drugs used simultaneously or in combination with the composition of the present disclosure, and other factors known in the medical field. The pharmaceutical composition of the present disclosure can be administered alone or in combination with other publicly-known anticancer drugs or components known as known as having an anticancer activity. It is important to administer the composition in the minimum amount that can exhibit the maximum effect without causing side effects, in consideration of all the above factors.

The pharmaceutical composition of the present disclosure can be administered such that the dosage per day is, for example, about 10 mg/kg to about 1,000 mg/kg, about 10 mg/kg to about 500 mg/kg, about 10 mg/kg to about 250 mg/kg, about 10 mg/kg to about 200 mg/kg, about 10 mg/kg to about 100 mg/kg, about 1 mg/kg to about 100 mg/kg, about 1 mg/kg to about 75 mg/kg, about 1 mg/kg to about 50 mg/kg, about 1 mg/kg to about 25 mg/kg, or about 1 mg/kg to about 10 mg/kg. The administration frequency of the composition can be, but is not particularly limited to, once, twice, three times, four times, etc. divided doses a day.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the active agent described herein are administered to a patient susceptible to or otherwise at risk of cancer. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the active agent described herein can be administered chronically, that is, for an extended period of time, including throughout the duration of the patient's life in order to ameliorate or otherwise control or limit the symptoms of the patient's disease or condition.

The amount of a given agent that will correspond to such an amount will vary depending upon factors such as the particular compound, disease condition and its severity, the identity (e.g., age, weight, gender, etc.) of the subject or host in need of treatment, but can nevertheless be routinely determined in a manner known in the art according to the particular circumstances surrounding the case, including, e.g., the specific agent being administered, the route of administration, the condition being treated, and the subject or host being treated.

In some embodiments, the methods further comprise administering a second active agent, such as cytotoxic agents, e.g., 5-FU, Methotrexate, Irinotecan, Docetaxel, Paclitaxel, Carboplatin, Oxaliplatin, targeted agents, e.g., Sunitinib, Sorafenib, Lapatinib, Imatinib, Erlotinib, Gefitinib, Trastuzumab (Herceptin), Everolimus, carbonic anhydrase inhibitor (CAi), monocarboxylate transporter inhibitor (MCTi), hormonal drugs, and cell therapies.

In some embodiments, the methods comprise administering a second anticancer agent such as USFDA approved drugs known in the art for cancer treatment including but are not limited to the following:

| Drug name | Indications | Mode of action |
| --- | --- | --- |
| Bavencio (avelumab) | Merkel cell carcinoma | programmed death ligand-1 (PD-L1) blocking antibody |
| Kisqali (ribociclib) | breast cancer | inhibitor of cyclin-dependent kinase (CDK) 4 and 6 |
| Olmutinib | non-small cell lung cancer | Covalently bonding to a cysteine residue near the kinase domain of epidermal growth factor receptor |
| Xermelo (telotristat ethyl) | carcinoid syndrome diarrhea | a tryptophan hydroxylase inhibitor |
| Zejula (niraparib) | primary peritoneal cancer | poly(ADP-ribose) polymerase (PARP) inhibitor |
| Cabometyx (cabozantinib) | renal cell carcinoma | tyrosine kinase inhibitor |
| Keytruda (pembrolizumab) | head and neck squamous cell cancer | programmed death receptor-1 (PD-1)-blocking antibody |
| Lartruvo (olaratumab) | soft tissue sarcoma | platelet-derived growth factor receptor alpha (PDGFR-α) blocking antibody |
| Lenvima (lenvatinib) | renal cell carcinoma | receptor tyrosine kinase (RTK) inhibitor |
| Opdivo (nivolumab) | classical Hodgkin lymphoma | blocking the cellular pathway known as PD-1/PD-L1 |
| Opdivo (nivolumab) | recurrent or metastatic squamous cell carcinoma of the head and neck | programmed death receptor-1 (PD-1) blocking antibody |
| Rubraca (rucaparib) | ovarian cancer and deleterious germline or somatic BRCA mutation | poly (ADP-ribose) polymerase (PARP) inhibitor |
| Sustol (granisetron) | prevention of chemotherapy-induced nausea and vomiting | serotonin-3 (5-HT3) receptor antagonist |
| Syndros (dronabinol oral solution) | anorexia associated with AIDS and nausea and vomiting associated with cancer chemotherapy | orally administered liquid formulation of the pharmaceutical cannabinoid dronabinol, a pharmaceutical version of tetrahydrocannabinol ("THC") |
| Tecentriq (atezolizumab) | urothelial carcinoma and metastatic non-small cell lung cancer | programmed death-ligand 1 (PD-L1) blocking antibody |
| Venclexta (venetoclax) | chronic lymphocytic leukemia with 17p deletion | BCL-2 inhibitor |
| Alecensa (alectinib) | ALK-positive, metastatic non-small cell lung cancer | tyrosine kinase inhibitor |
| Cotellic (cobimetinib) | BRAF V600E or V600K melanoma | tyrosine kinase inhibitor |
| Darzalex (daratumumab) | multiple myeloma | human CD38-directed monoclonal antibody |
| Empliciti (elotuzumab) | multiple myeloma patients who have received prior therapies | SLAMF7-directed immunostimulatory antibody |
| Farydak (panobinostat) | Multiple myeloma | histone deacetylase inhibitor |
| Ibrance (palbociclib) | ER-positive, HER2-negative breast cancer | pyridopyrimidine-derived cyclin-dependent kinase (CDK) inhibitor |
| Imlygic (talimogene laherparepvec) | unresectable recurrent melanoma | genetically modified oncolytic viral therapy |
| Keytruda (pembrolizumab) | PD-L1 positive advanced non-small cell lung cancer | blocking the cellular pathway known as PD-1/PD-L1 |
| Lenvima (lenvatinib) | thyroid cancer | receptor tyrosine kinase (RTK) inhibitor |
| Lonsurf (trifluridine and tipiracil) | metastatic colorectal cancer | trifluridine, a nucleoside metabolic inhibitor, and tipiracil, a thymidine phosphorylase inhibitor |
| Ninlaro (ixazomib) | Multiple myeloma | proteasome inhibitor |
| Odomzo (sonidegib) | locally advanced basal cell carcinoma | hedgehog pathway inhibitor |

-continued

| Drug name | Indications | Mode of action |
|---|---|---|
| Onivyde (irinotecan liposome injection) | metastatic pancreatic cancer | topoisomerase inhibitor |
| Opdivo (nivolumab) | renal cell carcinoma | blocking the cellular pathway known as PD-1/PD-L1 |
| Opdivo (nivolumab) | metastatic squamous non-small cell lung cancer | human monoclonal antibody that blocks the interaction between PD-1 and its ligands, PD-L1 and PD-L2 |
| Portrazza (necitumumab) | metastatic squamous non-small cell lung cancer | epidermal growth factor receptor (EGFR) antagonist |
| Tagrisso (osimertinib) | EGFR T790M mutation positive non-small cell lung cancer | EGFR-TKI, a targeted cancer therapy |
| Unituxin (dinutuximab) | pediatrics with high-risk neuroblastoma | chimeric monoclonal antibody |
| Varubi (rolapitant) | chemotherapy-induced nausea and vomiting | substance P/neurokinin 1 (NK1) receptor antagonist |
| Varubi (rolapitant) | chemotherapy-induced nausea and vomiting | a substance P/neurokinin 1 (NK1) receptor antagonist |
| Vistogard (uridine triacetate) | fluorouracil or capecitabine overdose | pyrimidine analog |
| Yondelis (trabectedin) | liposarcoma or leiomyosarcoma | alkylating agent |
| Akynzeo (netupitant and palonosetron) | chemotherapy-induced nausea and vomiting | netupitant, a substance P/neurokinin 1 (NK1) receptor antagonist, and palonosetron, a serotonin-3 (5-HT3) receptor antagonist |
| Beleodaq (belinostat) | relapsed or refractory peripheral T-cell lymphoma | histone deacetylase inhibitor |
| Blincyto (blinatumomab) | Philadelphia chromosome-negative relapsed/refractory B cell precursor acute lymphoblastic leukemia | Immunotherapy |
| Cyramza (ramucirumab) | gastric cancer | recombinant human IgG1 monoclonal antibody |
| Imbruvica (ibrutinib) | chronic lymphocytic leukemia | selective inhibitor of Bruton's tyrosine kinase (Btk) |
| Kadcyla (ado-trastuzumab emtansine) | HER2-positive metastatic breast cancer | HER2-targeted antibody-drug conjugate |
| Lynparza (olaparib) | previously treated BRCA mutated advanced ovarian cancer | a poly (ADP-ribose) polymerase (PARP) inhibitor |
| Opdivo (nivolumab) | unresectable or metastatic melanoma | a human immunoglobulin G4 (IgG4) monoclonal antibody that binds to the PD-1 receptor and blocks its interaction with PD-L1 and PD-L2, releasing PD-1 pathway-mediated inhibition of the immune response, including the anti-tumor immune response |
| Zydelig (ideialisib) | relapsed CLL, follicular B-cell NHL and small lymphocytic lymphoma | a small molecule inhibitor of phosphoinositide-3 kinase (PI3K) delta, an intracellular signaling component |
| Zykadia (ceritinib) | ALK+ metastatic non-small cell lung cancer | a highly selective inhibitor of anaplastic lymphoma kinase (ALK), a gene implicated in the development of some cancers |
| Gazyva (obinutuzumab) | previously untreated chronic lymphocytic leukemia | a monoclonal antibody that targets the CD20 antigen expressed on the surface of pre B- and mature B-lymphocytes |
| Gilotrif (afatinib) | metastatic non-small cell lung cancer with EGFR mutations | covalently binds to the kinase domains of EGFR (ErbB1), HER2 (ErbB2), and HER4 (ErbB4) and irreversibly inhibits tyrosine kinase autophosphorylation, resulting in downregulation of ErbB signaling |
| Imbruvica (ibrutinib) | mantle cell lymphoma | selective inhibitor of Bruton's tyrosine kinase (Btk) |
| Kadcyla (ado-trastuzumab emtansine) | HER2-positive metastatic breast cancer | a HER2-targeted antibody-drug conjugate |

-continued

| Drug name | Indications | Mode of action |
|---|---|---|
| Mekinist (trametinib) | unresectable or metastatic melanoma with BRAF V600E or V600K mutations | orally bioavailable inhibitor of mitogen-activated protein kinase kinase (MEK) with potential antineoplastic activity |
| Pomalyst (pomalidomide) | relapsed and refractory multiple myeloma | immunomodulatory antineoplastic agent |
| Revlimid (lenalidomide) | mantle cell lymphoma | immunomodulatory agent with antiangiogenic and antineoplastic properties |
| Stivarga (regorafenib) | gastrointestinal stromal tumor | potent oral multi-kinase inhibitor with a kinase inhibition profile targeting angiogenic, stromal and oncogenic receptor tyrosine kinases (TK) |
| Tafinlar (dabrafenib) | unresectable or metastatic melanoma with BRAF V600E mutation | inhibitor of some mutated forms of BRAF kinases, as well as wild-type BRAF and CRAF kinases |
| Valchlor (mechlorethamine) gel | Stage IA/IB mycosisfungoides-type cutaneous T-cell lymphoma | alkylating agent which inhibits rapidly proliferating cells |
| Xgeva (denosumab) | giant cell tumor of bone | human IgG2 monoclonal antibody that binds to human RANKL |
| Xofigo (radium Ra 223 dichloride) | prostate cancer with bone metastases | alpha particle-emitting pharmaceutical, is a radiotherapeutic drug |
| Abraxane (paclitaxel protein-bound particles for injectable suspension) | non-small cell lung cancer | intravenous nanoparticle, albumin-bound formulation of paclitaxel |
| Afinitor (everolimus) | renal angiomyolipoma associated with tuberous sclerosis complex | inhibitor of mTOR (mammalian target of rapamycin), a serine-threonine kinase, downstream of the PI3K/AKT pathway |
| Afinitor (everolimus) | hormone receptor-positive, HER2-negative breast cancer | inhibitor of mTOR (mammalian target of rapamycin), is an antineoplastic agent |
| Bosulif (bosutinib) | Ph+ chronic myelogenous leukemia | tyrosine kinase inhibitor |
| Cometriq (cabozantinib) | thyroid cancer | pan-tyrosine kinase inhibitor |
| Erivedge (vismodegib) | basal cell carcinoma | inhibitor of the hedgehog (Hh) signaling pathway |
| Iclusig (ponatinib) | chronic myeloid leukemia and Philadelphia chromosome positive acute lymphoblastic leukemia | small-molecule dual Abl/Src protein inhibitor |
| Inlyta (axitinib) | advanced renal cell carcinoma | tyrosine kinase inhibitor |
| Kyprolis (carfilzomib) | multiple myeloma | proteasome inhibitor |
| Marqibo (vinCRIStine sulfate LIPOSOME injection) | Ph- acute lymphoblastic leukemia | preventing chromosome segregation, triggering metaphase arrest and inhibition of mitosis |
| Neutroval (tbo-filgrastim) | severe chemotherapy-induced neutropenia | binds to G-CSF receptors and stimulates proliferation of neutrophil |
| Perjeta (pertuzumab) | HER2+ metastatic breast cancer | HER2/neu receptor antagonist compound |
| Picato (ingenol mebutate) gel | actinic keratosis | inducer of apoptosis (cell death) |
| Stivarga (regorafenib) | metastatic colorectal cancer | small molecule inhibitor of multiple membrane-bound and intracellular kinases |
| Subsys (fentanyl sublingual spray) | breakthrough cancer pain | opioid agonist whose principal therapeutic action is analgesia |
| Synribo (omacetaxine mepesuccinate) | chronic or accelerated phase chronic myeloid leukemia | synthesis inhibitor and is independent of direct Bcr-Abl binding |
| Votrient (pazopanib) | soft tissue sarcoma | vascular epidermal growth factor receptor (VEGFR) tyrosine kinase inhibitor |
| Xtandi (enzalutamide) | metastatic castration-resistant prostate cancer | androgen receptor inhibitor |

-continued

| Drug name | Indications | Mode of action |
|---|---|---|
| Zaltrap (ziv-aflibercept) | metastatic colorectal cancer | fusion protein specifically designed to bind all forms of Vascular Endothelial Growth Factor-A (VEGF-A) and Placental Growth Factor (PlGF) |
| Abstral (fentanyl sublingual tablets) | breakthrough cancer pain in opioid-tolerant patients | precise mechanism of the analgesic action is unknown |
| Adcetris (brentuximab vedotin) | Hodgkin lymphoma and anaplastic large cell lymphoma | antibody-drug conjugate comprised of an anti-CD30 antibody |
| Afinitor (everolimus) | advanced pancreatic neuroendocrine tumors | antineoplastic agent that works by inhibiting mammalian target of rapamycin (mTOR) |
| Erwinaze (asparaginase Erwinia chrysanthemi) | acute lymphoblastic leukemia | leukemic cells to synthesize asparagine due to lack of asparagine synthetase activity |
| Lazanda (fentanyl citrate) nasal spray | breakthrough cancer pain | nasal spray formulation of fentanyl citrate, a highly effective opiate analgesic |
| Sutent (sunitinib malate) | pancreatic neuroendocrine tumors | oral multi-kinase inhibitor and works by blocking multiple molecular targets |
| Sylatron (peginterferon alfa-2b) | Melanoma | covalent conjugate of recombinant alfa-2b interferon with monomethoxy polyethylene glycol (PEG) |
| Vandetanib (vandetanib) | thyroid cancer | receptor tyrosine kinase (RTK) inhibitor |
| Xalkori (crizotinib) | ALK+ non-small cell lung cancer | ATP-competitive small molecule dual inhibitor of mesenchymal epithelial transition growth factor (c-Met or hepatocyte growth factor) and ALK tyrosine kinases |
| Yervoy (ipilimurnab) | metastatic melanoma | recombinant, human monoclonal antibody that binds to the cytotoxic T-lymphocyte-associated antigen 4 (CTLA-4) |
| Zelboraf (vemurafenib) | BRAF + melanoma | selective inhibitor of the activated BRAFV600E gene |
| Zytiga (abiraterone acetate) | prostate cancer | orally active inhibitor CYP17 a cytochrome p450 complex |
| Halaven (eribulin mesylate) | metastatic breast cancer | non-taxane microtubule dynamics inhibitor |
| Herceptin (trastuzumab) | gastric cancer | humanized IgG1 kappa monoclonal antibody that selectively binds with high affinity to the extracellular domain of the human epidermal growth factor receptor 2 protein (HER2) |
| Jevtana (cabazitaxel) | prostate cancer | disrupting the microtubular network |
| Provenge (sipuleucel-T) | hormone refractory prostate cancer | autologous cellular immunotherapy designed to induce an immune response targeted against PAP (prostatic acid phosphatase) |
| Xgeva (denosumab) | prevention of skeletal-related events in patients with bone metastases from solid tumors | human IgG2 monoclonal antibody that binds to human RANKL |
| Zuplenz (ondansetron oral soluble film) | post-operative, chemotherapy and radiotherapy induced nausea and vomiting | a selective 5-HT3 receptor antagonist |
| Afinitor (everolimus) | renal cell carcinoma | inhibitor of mTOR (mammalian target of rapamycin), a serine-threonine kinase, downstream of the PI3K/AKT pathway |
| Arzerra (ofatumumab) | chronic lymphocytic leukemia | an anti-CD20 monoclonal antibody |
| Avastin (bevacizumab) | renal cell carcinoma | humanized antibody to vascular endothelial growth factor (VEGF) |
| Cervarix [Human Papillomavirus Bivalent (Types 16 and 18) Vaccine, Recombinant | prevention of cervical cancer and cervical intraepithelial neoplasia caused by HPV types 16 and 18 | a non-infectious recombinant, AS04-adjuvanted vaccine that contains recombinant L1 protein, the major antigenic protein of the capsid, of oncogenic HPV types 16 and 18 |
| Elitek (rasburicase) | management of plasma uric acid levels in adults with malignancies | a recombinant urate oxidase developed for the prevention and treatment of hyperuricemia in subjects receiving chemotherapy |

-continued

| Drug name | Indications | Mode of action |
| --- | --- | --- |
| Folotyn (pralatrexate injection) | peripheral T-cell lymphoma | a small molecule chemotherapeutic agent that inhibits dihdrofolate reductase (DHFR) |
| Istodax (romidepsin) | cutaneous T-cell lymphoma | histone deacetylase (HDAC) inhibitor |
| Onsolis (fentanyl buccal) | breakthrough cancer pain | precise mechanism of the analgesic action is unknown |
| Votrient (pazopanib) | renal cell carcinoma | a vascular epidermal growth factor receptor (VEGFR) tyrosine kinase inhibitor |
| Degarelix (degarelix for injection) | Prostate Cancer | a Gonadotropin-releasing hormone (GnRH) receptor antagonist |
| Fusilev (levoleucovorin) | For rescue after high-dose methotrexate therapy in osteosarcoma and to reduce the toxicity of methotrexate | the synthesis of purinic and pyrimidinic bases, the building blocks of DNA |
| Mozobil (plerixafor injection) | non-Hodgkin's lymphoma and multiple myeloma | a hematopoietic stem cell mobilizer and inhibitor of the CXCR4 chemokine receptor |
| Sancuso (granisetron) | chemotherapy-induced nausea and vomiting | a transdermal elective 5-hydroxytryptamine3 (5-HT3) receptor antagonist with little or no affinity for other serotonin receptors |
| Treanda (bendamustine hydrochloride) | Chronic lymphocytic leukemia and B-cell non-Hodgkin's lymphoma | rationally designed purine analog and alkylator hybrid |
| Evista (raloxifene hydrochloride) | the treatment/prevention of osteoporosis and reduction of breast cancer risk in postmenopausal women | estrogen agonist/antagonist, referred to as a selective estrogen receptor modulator |
| Hycamtin (topotecan hydrochloride) | small cell lung cancer | a semi-synthetic derivative of camptothecin and is an anti-tumor drug with topoisomerase I-inhibitory activity |
| Ixempra (ixabepilone) | Breast cancer | semi-synthetic analog of epothilone B |
| Tasigna (nilotinib hydrochloride monohydrate) | chronic myelogenous leukemia | signal transduction inhibitor of the Bcr-Abl kinase, c-kit and Platelet Derived Growth Factor (PDGF) |
| Torisel (temsirolimus) | renal cell carcinoma | derivative of rapamycin, an agent that exhibits antifungal, immunosuppressant and antitumor activities |
| Tykerb (lapatinib) | breast cancer | inhibitor of the intracellular tyrosine kinase domains of both Epidermal Growth Factor Receptor (EGFR [ErbB1]) and of Human Epidermal Receptor Type 2 (HER-2 [ErbB2]) receptors |
| Gardasil (quadrivalent human papillomavirus (types 6, 11, 16, 18) recombinant vaccine) | Cervical Cancer Caused by Human Papillomavirus | delivers HPV-6, -11, -16 and -18 L1 protein, conferring protection against these HPV strain |
| Sprycel (dasatinib) | Chronic Myeloid Leukemia | multiply-targeted tyrosine kinase inhibitor |
| Sutent (sunitinib) | Kidney Cancer/Gastrointestinal Stromal Tumors | orally-available small-molecule multiple receptor tyrosine kinase inhibitor |
| Vectibix (panitumumab) | colorectal cancer | recombinant, human IgG2 kappa monoclonal antibody that binds specifically to the human Epidermal Growth Factor Receptor (EGFR) |
| Arranon (nelarabine) | Lymphoblastic Leukemia | a cytotoxic deoxyguanosine analogue prodrug |
| Nexavar (sorafenib) | Renal Cell Carcinoma | a multikinase inhibitor targeting a number of serine/threonine and receptor tyrosine kinases |
| Alimta (pemetrexed for injection) | Mesothelioma | antifolate antineoplastic agent that exerts its action by disrupting folate-dependent metabolic processes essential for cell replication |
| Avastin (bevacizumab) | Colorectal Cancer | binds VEGF and prevents the interaction of VEGF to its receptors (Flt-1 and KDR) on the surface of endothelial cells |
| Clolar (clofarabine) | Lymphoblastic Leukemia | disrupts DNA synthesis and causes fatal replication errors through the disruption of several intracellular syntetic pathways |

-continued

| Drug name | Indications | Mode of action |
| --- | --- | --- |
| Erbitux (cetuximab) | Colorectal Cancer | injection is a monoclonal antibody hat targets and inhibits epidermal growth factor receptor (EGFR) |
| Sensipar (cinacalcet) | Hyperparathyroidism/ Hypercalcemia | increases the sensitivity of the calcium-sensing receptor to activation by extracellular calcium |
| Tarceva (erlotinib, OSI 774) | Non-small cell lung cancer | Human Epidermal Growth Factor Receptor Type 1/Epidermal Growth Factor Receptor (HER1/EGFR) tyrosine kinase inhibitor |
| Aloxi (palonosetron) | Chemotherapy side effects | injectable anti-vomiting and anti-nausea agent taken just chemotherapy treatments |
| Bexxar | Non-Hodgkin's Lymphoma | a murine IgG2a lambda monoclonal antibody directed against the CD20 antigen |
| Emend (aprepitant) | Chemotherapy-induced Nausea and Vomiting | P/neurokinin 1 (NK1) receptor antagonist |
| Iressa (gefitinib) | Non-Small-Cell Lung Cancer | anticancer drug that inhibits an enzyme (tyrosine kinase) |
| Plenaxis (abarelix for injectable suspension) | Prostate Cancer | a gonadotropin-releasing hormone (GnRH) antagonist |
| Premarin (conjugated estrogens) | prevention of postmenopausal osteoporosis and treatment of vasomotor menopause symptoms | oral administration contains a mixture of conjugated estrogens obtained exclusively from natural sources |
| UroXatral (alfuzosin HCl extended-release tablets) | Benign Prostatic Hyperplasia | selective antagonist of post-synaptic alpha1-adrenoreceptors |
| Velcade (bortezomib) | Multiple Myeloma | reversible inhibitor of the chymotrypsin-like activity of the 26S proteasome in mammalian cells |
| Eligard (leuprolide acetate) | Advanced prostate cancer | LH-RH agonist, acts as a potent inhibitor of gonadotropin secretion when given continuously in therapeutic dose |
| Eloxatin (oxaliplatin/5-fluorouracil/leucovorin) | Metastatic colon or rectum carcinomas that have recurred or progressed within six months folowing first-line treatment | organoplatinum alkylating agent that increases the tumor response rate to 5-FU/LV treatment |
| Faslodex (fulvestrant) | Hormone receptor positive metastatic breast cancer | estrogen receptor antagonist that binds to the estrogen receptor |
| Gleevec (imatinib mesylate) | Gastrointestinal stromal tumors (GISTs) | receptor tyrosine kinases for platelet-derived growth factor (PDGF) and stem cell factor (SCF), c-kit, and inhibits PDGF- and SCF-mediated cellular events |
| Neulasta | Neutropenia | protein that stimulates the production of neutrophils, a type of white blood cell that is depleted during cytotoxic chemotherapy |
| SecreFlo (secretin) | Pancreatic dysfunction and gastrinoma | non-pyrogenic, lypholized white cake powder acetate salt of secretin, a peptide hormone |
| Zevalin (ibritumomab tiuxetan) | Non-Hodgkin's lymphoma | complementarity-determining regions of Ibritumomab bind to the CD20 antigen on B lymphocytes |
| Zometa (zoledronic acid) | Multiple myeloma; bone metastases from solid tumors | inhibits osteoclastic activity and induces osteoclast apoptosis |
| Campath | Leukemia | binding to the CD52 antigen that is present on the surface of the malignant lymphocytes |
| Femara (letrozole) | Hormone receptor positive or hormone receptor unknown locally advanced or metastatic breast cancer | inhibits the conversion of androgens to estrogens |
| Gleevec (imatinib mesylate) | chronic myeloid leukemia | protein-tyrosine kinase inhibitor that blocks the constitutive abnormal tyrosine kinase, Bcr-Abl tyrosine kinas |
| Kytril (granisetron) solution | Nausea and vomiting associated with cancer therapy | selective 5-hydroxytryptamine3 (5-HT3) receptor antagonist |

-continued

| Drug name | Indications | Mode of action |
|---|---|---|
| Trelstar LA (triptorelin pamoate) | Prostate cancer | a potent repressor of gonadotropin secretion when given continuously and in therapeutic dosess |
| Xeloda | Oncology | first oral drug that works through enzymatic activation of the cancer fighting substance fluorouracil (5-FU) |
| Zometa (zoledronic acid) | Hypercalcemia of malignancy | pharmacologic action of zoledronic acid is inhibition of bone resorption |
| Mylotarg (gemtuzumab ozogamicin) | Acute Myeloid Leukemia (AML) | binds to the CD33 antigen |
| Trelstar Depot (triptorelin pamoate) | For the palliative treatment of advanced prostate cancer | potent repressor of gonadotropin secretion |
| Trisenox (arsenic trioxide) | Acute Promyelocytic Leukemia | The mechanism of action of Trisenox is not completely understood |
| Viadur (leuprolide acetate implant) | For the palliative treatment of advanced prostate cancer | LH-RH agonist, acts as a potent inhibitor of gonadotropin secretion |
| Aromasin Tablets | Treatment of advanced breast cancer in postmenopausal women whose disease has progressed following tamoxifen therapy | irreversible, steroidal aromatase inactivator |
| Busulflex | Oncology/Hematology | bifunctional alkylating agent |
| Doxil (doxorubicin HCl liposome injection) | Oncology | targeted delivery system called STEALTH technology |
| Ellence | Component of adjuvant therapy in patients with evidence of axillary node tumor involvement for primary breast cancer | anthracycline cytotoxic agent (the precise mechanisms of epirubicin's cytotoxic and/or antiproliferative properties have not been completely elucidated) |
| Ethyol (amifostine) | Oncology | reduce xerostomia in patients undergoing post-operative radiation treatment for head and neck cancer |
| Temodar | Oncology | oral cytotoxic alkylating agent |
| UVADEX Sterile Solution | Oncology | treatment of the skin manifestations of cutaneous T-cell lymphoma (CTCL) |
| Zofran | Oncology | prevention of chemotherapy and radiation-induced nausea and vomiting |
| Actiq | Oncology | medicine is absorbed through the lining of your mouth. From there, it goes into your bloodstream |
| Anzemet | prevention of nausea and vomiting associated with chemotherapy and surgery | prevents nausea and vomiting associated with chemotherapy and surgery |
| Camptosar | Oncology | Treatment of patients with metastatic carcinoma of the colon or rectum whose disease has recurred or progressed following 5-FU-based therapy |
| Gemzar (gemcitabine HCL) | Lung cancer | combination with cisplatin for the first-line treatment of patients with inoperable, locally advanced (Stage IIIA or IIIB) or metastatic (Stage IV) non-small cell lung cancer |
| Herceptin | Breast cancer | used as a second- or third-line therapy for patients with metastatic breast cancer |
| Inform HER-2/neu breast cancer test | breast cancer prediction | presence or absence of increased copies of the HER-2/neu gene |
| Neupogen | slow white blood cell recovery following chemotherapy | reduce the time to neutrophil recovery and the duration of fever following chemotherapy treatment |
| Nolvadex | Oncology | reduces the incidence of breast cancer in women at high risk for breast cancer |
| Photofrin | Non-sroall cell lung cancer | injection in treating early-stage, microinvasive lung cancer |
| Proleukin | Metastatic melanoma | injectable, recombinant form of interleukin-2 |
| Sclerosol Intrapleural Aerosol | malignant pleural effusions | prevention of recurrence of malignant pleural effusions in symptomatic patients |
| Valstar | Oncology | anthracycline that affects a variety of inter-related biological functions, most of which involve nucleic acid metabolism |

-continued

| Drug name | Indications | Mode of action |
| --- | --- | --- |
| Xeloda | breast cancer | |
| Zofran | postoperative vomiting and nausea in adults | postoperative nausea and vomiting in adults |
| Anzemet | Treatment for chemotherapy induced emesis | prevention of chemotherapy-induced nausea and vomiting, and prevention of postoperative nausea and vomiting |
| Bromfenac | acute pain | provides an alternative to opioids for the management of acute pain |
| Femara (letrozole) | breast cancer | second-line anti-estrogen therapy |
| Gliadel Wafer (polifeprosan 20 with carmustine implant) | brain cancer | the first brain cancer treatment to deliver chemotherapy directly to the tumor site |
| Intron A (interferon alfa-2b, recombinant) | non-Hodgkin's lymphoma | initial treatment of patients with clinically aggressive non-Hodgkin's lymphoma (NHL) |
| Kytril (grantsetron) tablets | nausea and vomiting associated with chemotherapy | treatment of nausea and vomiting associated with chemotherapy |
| Lupron Depot (leuprolide acetate for depot suspension) | prostate cancer | inhibiting the production of the hormone testosterone |
| Miraluma test | breast imaging | radiopharmaceutical that is thought to accumulate in areas of increased metabolic activity in malignant cells |
| Neumega | platelet deficiency | promote the production of the body's supply of platelets in cancer patients with solid tumors or lymphoma who are undergoing chemotherapy |
| Quadramet (Samarium Sm 153 Lexidronam Injection) | pain associated with bone cancer | targets the sites of new bone formation, concentrating in regions of the bone that have been invaded with metastatic tumor |
| Rituxan | non-hodgkin's lymphoma | chemically as rituximab, becomes the first monoclonal antibody sold in this country to treat cancer |
| Taxol | Kaposi's Sarcoma | reduces the size of patients' tumors and diminishes their symptoms and pain |
| Anexsia | chronic pain | treatment of chronic pain |
| Aredia (pamidronate disodium for injection) | osteolytic bone metastases of breast cancer | provide relief of bone pain caused by metastatic breast cancer, thereby reducing the need for narcotic analgesics |
| Arimidex (anastrozole) | post menopausal breast cancer | first entry in a new class of third-generation selective oral aromatase inhibitors |
| Campostar | metastatic colorectal cancer | treatment of metastatic colorectal cancer that has recurred or progressed after standard therapy with the anticancer agent fluorouracil. |
| CEA-Scan | colorectal cancer | antibody fragment (Fab') against the tumor marker, carcinoembryonic antigen ("CEA") |
| Elliotts B Solution (buffered intrathecal electrolyte/dextrose injection) | meningeal leukemia or lymphocytic lymphoma | erebrospinal fluid in pH, electrolyte composition, glucose content, and osmolarity |
| Eulexin (flutamide) | prostate cancer | a class of drugs known as anti-androgens, which act by directly blocking the cancer-promoting activities of androgens, or male sex hormones, of which the principal one is testosterone |
| Feridex I.V. | liver cancer | contrast agent for magnetic resonance imaging (MRI) of liver lesions |
| GastroMARK | gastrointestinal forms of cancer | a magnetic resonance imaging agent for the gastrointestinal tract |
| Gemzar (gemcitabine HCL) | pancreatic cancer | a nucleoside analogue that mimics a natural building block of DNA |
| Hycamtin (topotecan hydrochloride) | ovarian cancer | the first topoisomerase I inhibitor |
| Kadian | chronic pain | provides relief for chronic moderate to severe pain (pain related to cancer) |
| Leukine (sargramostim) | replenishment of white blood cells, fungal infections | helps older adult leukemia subjects' white blood cells recover quickly, and it helps prevent life-threatening infections, including fungal infections, which often complicate their recovery and increase their risk of complications |

| Drug name | Indications | Mode of action |
| --- | --- | --- |
| Lupron Depot (leuprolide acetate for depot suspension) | prostate cancer | shutting down the production of the hormone testosterone, which plays a significant role in the growth of prostate cancer |
| Photodynamic Therapy | esophageal cancer | combination with laser light of a specific wavelength and fiberoptic delivery devices to kill cancerous cells selectively |
| Taxotere (Docetaxel) | breast cancer | inhibits cancer cell growth depends on the formation of an internal cellular skeleton made up of elements called microtubules |
| UltraJect | chronic pain | treat moderate to severe pain such as that associated with post-operative surgical pain or cancer |
| Visipaque (iodixanol) | diagnosis of disease in major organs | a contrast agent that allows doctors to better diagnose diseases of the heart, brain, kidney, blood vessels and other major organs |
| Zoladex (10.8 mg goserelin acetate implant) | prostate cancer | analogue of naturally occurring LHRH |
| Ethyol (amifostine) | ovarian cancer | reduce the renal toxicity associated with repeated administration of chemotherapy |
| Intron A (Interferon alfa-2b, recombinant) | malignant melanoma | exact mechanism of action is unknown |
| Leukine (sargramostim) | Transplantation | white blood cells after autologous and allogeneic bone marrow transplantation as well as after peripheral blood progenitor cell (PBPC) transplantation |

The invention also includes:

A. A sustained-release pharmaceutical composition comprising an anticancer agent as a pharmaceutically active ingredient, wherein the sustained-release pharmaceutical composition comprises at least one substance selected from the group consisting of polymers, polysaccharides, and lipids.

B. The composition according to A, wherein the anticancer agent is calcium lactate.

C. The composition according to A, wherein the polymer is a poloxamer series, polyvinylpyrrolidone, polyethylene glycol (PEG), or polyglycolic lactic acid (PLGA).

D. The composition according to A, wherein the polysaccharide is at least one polysaccharide selected from the group consisting of cellulose derivatives, pectin, hyaluronic acid, starch, guar gum, chitosan, gelatin, collagen and alginic acid.

E. The composition according to A, wherein the lipid is selected from the group consisting of mono- or tri-fatty acid glycerin esters and polyethylene glycol complexes thereof, polyethylene glycol esters of vegetable oils, and fatty acid propylene glycol esters; Sesame oil, soybean oil, castor oil, corn oil, palm oil, peanut oil, cacao oil, cottonseed oil, sunflower seed oil, safflower oil, almond oil, olive oil and hydrogenated oils thereof; but are not limited to, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate and cetyl palmitate; and at least one component selected from the group consisting of lauryl alcohol, oleyl alcohol, cetyl alcohol and stearyl alcohol.

F. The composition according to A, wherein the weight ratio of the anticancer agent to the polymer of the composition is in the range of 1:2 to 1:10.

G. The composition according to A, wherein the weight ratio of the anticancer agent:polysaccharide of the composition is in the range of 1:0.5 to 1:10.

H. The composition according to A, wherein the weight ratio of the anticancer agent:polysaccharide:polymer of the composition is in the range of 1:0.5:2 to 1:10:10.

I. The composition according to A, wherein the weight ratio of the anticancer agent:polysaccharide:lipid:polymer of the composition is in the range of 1:0.5:1:2 to 1:10:100:10.

J. The composition according to any one of A-I, wherein the composition is for administration by an injection or oral mucosa.

K. A sustained-release pharmaceutical composition comprising an anticancer agent as a pharmaceutically active ingredient, wherein the anticancer agent is coated with at least one member selected from the group consisting of hydroxypropyl methyl cellulose phthalate (HPMCP), cellulose acetate phthalate (CAP), polyvinyl acetate phthalate (PVAP), shellac, and polymer of methacrylic acid and an ester thereof.

L. The composition according to claim K, wherein the anticancer agent is calcium lactate.

EXAMPLES

Calcium lactate is also referred to herein as OMT-110 or OMT110.

Example 1

Calcium lactate was dissolved in water and the solution was maintained at 4° C. for 15 minutes and Poloxamer 407 (Sigma-Aldrich, Germany) was added to the solution. The mixture was stored until a clear solution was obtained. (Composition: calcium lactate: 400 mg, Poloxamer 407: 2.5 g, Water: 10 g.)

Example 2

Calcium lactate was dissolved in water. Methylcellulose (MC) (DAEJUNG, South Korea) was added to the solution, and the mixture was stirred and maintained at room temperature until methylcellulose was completely dissolved and then kept at 4° C. for 15 minutes. (Composition: calcium lactate: 400 mg, MC: 2.5 g, Water: 10 g.) Example 3

Calcium lactate is dissolved in water, MC is added to the solution, the mixture is stirred and maintained at room temperature until the MC is completely dissolved, then kept at 4° C. for 15 minutes and Poloxamer 407 is added to the solution. The mixture was stored until a clear solution was obtained. (Composition: calcium lactate: 400 mg, MC: 200 mg, Poloxamer 407: 2.5 g, Water. 10 g.) Example 4

Calcium lactate was dissolved in water, and MC and corn oil (DAEJUNG, South Korea) were added to the solution. The mixture was stirred and maintained at room temperature until MC was completely dissolved, kept at 4° C. for 15 minutes, and Poloxamer 407 was added to the solution and the mixture was stored until a clear solution was obtained. (Composition: calcium lactate: 400 mg, MC: 200 mg, corn oil: 400 mg, Poloxamer 407: 2.5 g, water: 10 g.)

Example 5

Pectin (Sigma-Aldrich, Germany) was dissolved in water, and the mixture was stirred and kept at room temperature until the pectin was completely swollen. $CaCl_2$ was added and dissolved by stirring and calcium lactate was added and stirred until a homogenized mixture was obtained. (Composition: calcium lactate: 400 mg, $CaCl_2$: 150 mg, pectin: 200 mg, water: 10 g.)

Example 6

Alginic acid (Sigma-Aldrich, Germany) was dissolved in water, and the mixture was stirred and maintained at room temperature until complete swelling occurred. $CaCl_2$ was added to the solution and dissolved by stirring and calcium lactate was added until a homogenized mixture was obtained. (Composition: calcium lactate: 400 mg, $CaCl_2$: 150 mg, alginate: 200 mg, water: 10 g.)

Example 7

The pectin was dissolved in water, the mixture was stirred and kept at room temperature until the pectin swelled completely, then calcium lactate was added and stirred to obtain a homogenized mixture. (Composition: calcium lactate: 400 mg, pectin: 200 mg, water: 10 g.)

Example 8

Alginic acid was dissolved in water, and the mixture was stirred and kept at room temperature until complete swelling and calcium lactate was added and stirred to obtain a homogenized mixture. (Composition: calcium lactate: 400 mg, alginate: 200 mg, water: 10 g.)

Example 9: Drug Release Experiment

Dissolution tester method: Elution Tester (Labfine Co., Mumbai, India); Temperature: 37° C.; stirring: 300 rpm; membrane: Whatman 0.45 μm, nylon.
Release study: 2 g of the formulations of Examples 1 to 8 above were weighed and added to the donor component. The receptor components were filled with distilled water and the cells were set in the system for a total volume of 200 ml at pH 6.8. At each sampling time, 0.5 ml of release medium was removed and replaced with distilled water. All experiments were repeated 3 times. The results of drug release follows.

As shown in FIG. 1, in the formulations of Examples 1 and 2 prepared according to the present invention, it is confirmed that the drug is completely released within 6 to 24 hours. In comparison, in the formulations of Examples 3 and 4, it can be seen that the drug is continuously released up to 144 hours. This suggests that methylcellulose and lipid (corn oil) are properly mixed with poloxamer 407 to slow the diffusion of drug in the hydrogel, thereby achieving sustained release.

Figure 2:
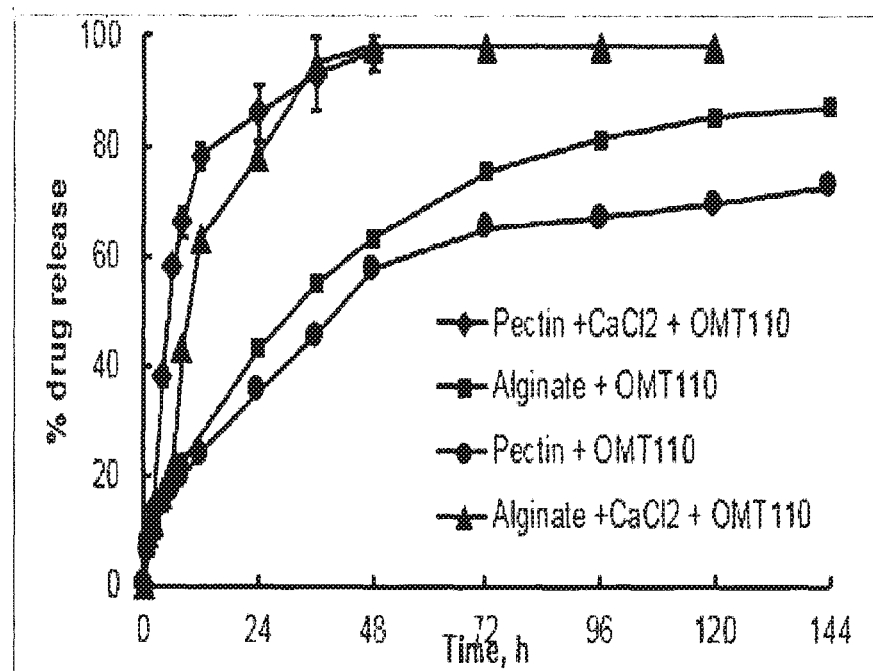

As shown in FIG. 2, the drug is completely released within 6 to 24 hours in the hydrogels of Examples 5 and 6 prepared according to the present invention. In comparison, in the hydrogels of Examples 7 and 8, it was confirmed that the drug was continuously released up to 144 hours. Without being bound by any theory, it is believed that the calcium lactate is incorporated into pectin and alginate to form a sustained-release drug delivery system by forming gelation using calcium lactate, which is a Ca ion salt and not a Ca ion.

Example 10: Design and Evaluation of New Enteric Coating Formulations of Calcium Lactate Calcium lactate was found to exhibit strong anti-cancer effects in vitro. However, the drug is very unstable in water, especially under acidic conditions, and rapidly degraded. Therefore, it is difficult for this drug to show pharmaceutical efficacy with a general oral formulation because it is readily decomposed in the acidic environment of the stomach upon oral administration. Calcium lactate is also not absorbed when it reaches the large intestines because it is destroyed by enzymes present in the large intestine.

The purpose of this study was to formulate enteric-coated calcium lactate preparation for the purpose of protecting the drug in the stomach and being absorbed in the small intestines before reaching the large intestines.

Two separate preparations have been developed to obtain enteric-coated calcium lactate and the products were evaluated by a dissolution test. In the first preparation, a pellet containing calcium lactate was prepared using a fluidized-bed coater, enteric-coated, and filled into a capsule. In the second preparation, the fast-dissolving tablet of 100 mg of calcium lactate was prepared and enteric-coated. As the enteric coating layer becomes thicker, the acid resistance is better, but the absorption is not complete in the small intestine as the disintegration of the preparation is delayed. Therefore, to obtain the optimal enteric coating layer, the formulation is evaluated with respect to acid resistance and disintegration rate while changing the content of the enteric-coating solution.

A) Reagents and Materials (1) Reagents
The following reagents were purchased and used without further purification.
  Calcium lactate (provided by Metimedi Pharmaceuticals Co. Ltd.,)
  HPMCP (pH 5.0, 5 cps, Shinetsu, Japan)
  HPMCP (pH 5.5, 5 cps, Shinetsu, Japan)
  Polyvinyl acetate phthalate (Opadry enteric 91 series, Colorcon, USA)
  Microcrystalline cellulose (Vivapur 12, JRS Pharma, Germany)
  Water was used after filtration by reverse osmosis in the laboratory and all other reagents were reagent grade.

(2) Equipment
The following equipment were used.
HPLC system (Agilent, Model 1260 Infinity)
Balance (Mettler Toledo, Model ML802)
Balance (Sartorius, Model Quintix224-1SKR)
pH meter (Mettler Toledo, Model FiveEasy Plus)
Isothermal water bath (Daihan, Model Maxturdy-30)
Sonicator (Branson, Model 2510)
Disintegration tester (Erweka, Model ZT 222)
Fluid-bed coater (Enger, China, Model Labcoat II)
Tableting machine (Erweka, Germany, Model EP-1)
Coater (Freund Industrial, Japan, Model HOT-MINI)
Dissolution tester (Labfine, Model DST-810)
B) Analysis of Calcium Lactate
The amount of calcium lactate in the samples was analyzed by a HPLC method developed in this laboratory. This HPLC method was validated according to the ICH Guideline of Q2 (R1) for linearity, intraday and interday precision and accuracy.
  (1) HPLC System (Agilent, Model 1260 Infinity)
  Quaternary pump (Agilent, Model G1311C)
  Auto-sampler (Agilent, Model G1329B)
  UV detector (Agilent, Model G1314F)
  OpenLAB Chromatography Data System (Agilent, Model CDS)
  (2) HPLC Analysis Conditions
  Mobile phase: $H_2SO_4$ 7.5 mM
  Flow rate: 0.6 ml/min
  Column: Rezex RHM-Monosaccharide-$H^+$ column (5 μm, 7.8 mm×300 mm, Phenomenex, USA)
  Column temperature: 40° C.
  Detection wavelength: 210 nm
  Injection volume: 10 μl
  Retention time: About 14 mins.
C) Solubility of Calcium Lactate in Various Solvents
The solubility of calcium lactate in various solvents was measured using Higuchi and Connors method. An excess amount of calcium lactate (pentahydrate form and dried form) was placed in a small vial containing purified water or organic solvents. The vials were then sealed and mounted in a constant-temperature water bath and shaken at 50 rpm at 30° C. for 72 hours. Shaking for 72 hours was found to be sufficient for solubility measurements as a preliminary experiment. After shaking, the sample was filtered with 0.45 μm membrane filter (Whatman, nylon filter), and diluted appropriately with purified water, and analyzed using HPLC method. This experiment was repeated three times.
The dried form of calcium lactate was obtained by drying 30.81 g of calcium lactate pentahydrate form in an oven at 100° C. As a preliminary experiment, the weight of calcium lactate was measured after 8, 24, 48, and 72 hours of drying and it was found that the final weight was reached after 24 hours. The moisture content of the dried form of calcium lactate was 4.05% (w/w).
D) Preparation of enteric-coated pellets of calcium lactate
In order to make calcium lactate be absorbed as quickly and readily as possible, the drug should be completely protected from the acidic environment of the stomach and the preparation should be immediately disintegrated as soon as it reaches the small intestine and to release the drug for absorption.
The enteric-coated pellets were prepared using a fluid-bed coater at the factory of Natural Way Co. The preparation process of the enteric-coated pellet of calcium lactate was as follows.
First, calcium lactate was screened with 60 mesh sieve. Approximately 15% of the calcium lactate was passed through the sieve and the remaining 85% was used for the preparation. These fine granules were put into a fluidized-bed coater and enteric-coated until a weight gain of 45%, 60%, and 100% were achieved relative to the weight of fine granules under the following operating and coating conditions.
  (1) Preparation of Enteric-Coating Solution
  Contents of enteric coating solution (5% solid content)

| | |
|---|---|
| HPMCP | 95 |
| glycerin | 5 |
| ethanol | 95 |
| water | 5 |

95 g of HPMCP (pH 5.5) and 5 g of glycerin were added to a solution of ethanol:water (95:5 mixture) while stirring and dissolved to prepare an enteric-coating solution.
  Operating conditions of fluidized-bed coater
  type of spray: bottom spray
  batch size: 300 g
  nozzle type: round
  number of nozzle: 1
  nozzle diameter: 0.8 mm
  air cap: standard
  pump type: peristaltic
  column diameter: 12 cm
  column height: 2.5 cm
  number of column: 1
  Coating Conditions of Fluidized-Bed Coater
  inlet warm up temperature: 32° C.
  warm up time: 3 minutes
The detailed coating conditions are shown in Table 1.

TABLE 1

Condition of enteric-coating used for fluid-bed coater

| Coating number* | time min | inlet temp (° C.) | exhaust temp (° C.) | product temp (° C.) | spray rate (g/min) | aap** (psi) | rotor speed (RPM) | air velocity (m/s) | balance reading (g) |
|---|---|---|---|---|---|---|---|---|---|
| CN1 | 3 | 85 | 27.6 | 34.8 | | 2.5 | 10 | 30 | 0 |
| | 10 | 96 | 28 | 34.7 | 12.6 | 2.5 | 15 | 35 | 88 |
| | 20 | 96 | 30.3 | 36.7 | 16.6 | 2.5 | 19 | 35 | 254 |
| | 30 | 96 | 31.4 | 37.5 | 19 | 2.5 | 22 | 40 | 444 |
| | 40 | 96 | 32.2 | 37.7 | 20 | 2.5 | 22 | 40 | 644 |
| | 50 | 96 | 32 | 36.2 | 23 | 2.7 | 26 | 42 | 874 |
| | 60 | 96 | 33 | 37.3 | 22.6 | 2.7 | 26 | 42 | 1100 |
| | 70 | 90 | 34 | 37.8 | 22.4 | 2.8 | 27 | 45 | 1324 |
| | 80 | 85 | 33.6 | 37.3 | 24 | 3 | 27 | 47 | 1564 |
| | 90 | 80 | 35 | 39.9 | 23.6 | 3 | 27 | 50 | 1800 |

TABLE 1-continued

Condition of enteric-coating used for fluid-bed coater

| Coating number* | time min | inlet temp (° C.) | exhaust temp (° C.) | product temp (° C.) | spray rate (g/min) | aap** (psi) | rotor speed (RPM) | air velocity (m/s) | balance reading (g) |
|---|---|---|---|---|---|---|---|---|---|
| | 100 | 80 | 34.5 | 37.7 | 24.1 | 3 | 27 | 53 | 2041 |
| | 110 | 96 | 28 | 37.9 | 24.3 | 3 | 27 | 53 | 2284 |
| | 128 | 96 | 30.3 | 38.1 | 23.4 | 3 | 27 | 53 | 2706 |
| CN2 | 10 | 80 | 30.5 | 35.4 | −21.7 | 3 | 15 | 40 | 150 |
| | 20 | 80 | 31.2 | 36.5 | 19.5 | 3 | 17 | 45 | 345 |
| | 30 | 75 | 32.2 | 37.1 | 19.6 | 3 | 17 | 45 | 541 |
| | 40 | 75 | 33.3 | 37.7 | 19.8 | 3 | 17 | 45 | 739 |
| | 50 | 75 | 33.2 | 36.2 | 20.2 | 3 | 19 | 46 | 941 |
| | 60 | 75 | 33.5 | 37.3 | 20.7 | 3 | 19 | 50 | 1148 |
| | 70 | 70 | 33.6 | 37.8 | 19.7 | 3 | 19 | 52 | 1345 |
| | 80 | 65 | 33.6 | 37.3 | 20.8 | 3 | 19 | 55 | 1553 |
| | 90 | 65 | 34.1 | 39.9 | 20.2 | 3 | 19 | 57 | 1755 |
| | 100 | 73 | 34.2 | 39.2 | 20 | 3 | 21 | 60 | 1955 |
| | 110 | 70 | 34.5 | 35.4 | 21 | 3 | 21 | 60 | 2165.4 |
| CN3 | 10 | 80 | 31 | 35.4 | −19.6 | 3 | 21 | 45 | 210 |
| | 20 | 80 | 31.2 | 36.7 | 19.5 | 3 | 21 | 45 | 405 |
| | 30 | 80 | 32.6 | 37.5 | 19.3 | 3 | 21 | 45 | 598 |
| | 40 | 80 | 33 | 37.7 | 19.6 | 3 | 21 | 45 | 794 |
| | 50 | 85 | 33 | 36.2 | 19.1 | 3 | 21 | 45 | 985 |
| | 60 | 80 | 34 | 37.3 | 20.3 | 3 | 22 | 45 | 1188 |
| | 70 | 80 | 33.8 | 37.8 | 20.9 | 3 | 22 | 45 | 1397 |
| | 80 | 80 | 34.2 | 37.3 | 20.3 | 3 | 22 | 45 | 1600 |
| | 90 | 80 | 34.1 | 37.3 | 20.3 | 3 | 22 | 45 | 1803 |
| | 100 | 80 | 34.2 | 37.6 | 20.2 | 3 | 22 | 45 | 2005 |

*coating number: weight % of enteric-coated granule against core, CN1: 45%. CN2: 60%, CN3: 100%
**atomizing air pressure E) Preparation of Enteric-Coated Tablets of Calcium Lactate Usually, a tablet has a relatively long disintegration time. However, the same goal of the pellets can be obtained when the tablet is protected under acidic conditions of the stomach, and disintegrated immediately upon reaching the small intestines for rapid absorption in the small intestines. Based on this fact, fast-dissolving tablets of calcium lactate were prepared, and enteric-coated. The preparation process of calcium lactate enteric-coated tablets was as follows.

Calcium lactate tablets were prepared by direct compression method using a tableting machine (Erweka, Model: EP-1) and 8 mm concave punch. The preparation batch size was 250 tablets. The detailed formulation of calcium lactate is shown in Table 2.

TABLE 2

Formulation of calcium lactate tablet

| Component | Amount | Remark |
|---|---|---|
| Calcium lactate | 100 mg | API |
| Vivapur 12 | 49.25 mg | Filler |
| Magnesium stearate | 0.75 mg | lubricant (0.5%) |
| Total | 150 mg | |

First, 25 g of calcium lactate and 12.312 g of Vivapur 12 were weighed using a balance (Mettler Toledo, Model: ML802) and thoroughly mixed. Next, 0.187 g of magnesium stearate was weighed using a balance (Sartorius, Model: Quintix 224-1SKR) and added to the mixture. This final mixture was compressed using 8 mm concave punch under the following conditions. The hardness was adjusted to 80-100 N.

F) Measurement of Physical Properties of Prepared Tablets

Hardness was measured with a hardness tester (Erweka, Model: TBH 125) using ten tablets. The weight of the tablets was measured with a balance (Sartorius, Model: Quintix 224-1SKR) using ten tablets. The disintegration test of the prepared enteric-coated tablets was carried out using a disintegration tester according to the pharmacopoeia methods. The specifications of the calcium lactate tablets thus measured are shown in Table 3.

TABLE 3

Specifications of calcium lactate tablet

| Specification | Result | Remark |
|---|---|---|
| Size (diameter) | 8 mm | |
| Thickness | 4-4.5 mm | |
| Hardness | 81-85 N | n = 10 |
| Disintegration | <3 minute | n = 6 |
| Average weight | 149.2 ± 0.8 mg | n = 10 |

G) Enteric-Coating of Tablets

The tablets were coated with the enteric-coating solution shown in Table 4 using a coater (Freund Industrial Co., Model: HOT-MINI) equipped with a pump (Eyela, Model: SMP-4). Polyvinyl acetate phthalate (Opadry enteric 91 series) was used as the enteric-coating agent.

TABLE 4

Formula of enteric-coating base

| Component | Content, % | Remarks |
|---|---|---|
| Polyvinyl acetate phthalate | 66.682 | (Coating agent) |
| Talc | 13.327 | (Lubricant) |
| Purified stearic acid | 13.327 | (Lubricant) |
| Triethyl citrate | 6.664 | (Plasticizer) |
| Total | 100 | |

(1) In a 1 liter beaker, 300 ml of isopropanol and 200 ml of methylene chloride were placed and mixed using a magnetic stirrer for about 10 min.

(2) Into the solvent prepared in (1), 30 g of polyvinyl acetate phthalate was added and stirred for about 1 hour.

(3) After passing the solution through a 100 mesh sieve, the passed materials were stirred.

Next, coating was carried out under the following conditions with this enteric-coating solution.
- inlet temperature: 65-70° C.
- outlet temperature: 30-33° C.
- product temperature: 30-32° C.
- Injection speed: 1.7 ml/min
- air: 0.1 MPa
- RPM: 12-16

Samples of the coated tablets were taken during the coating when the tablets weight were increased to about 2%, 5%, 8%, and 10%.

G) Dissolution Test of Enteric-Coated Calcium Lactate

The dissolution tests of enteric pellets and tablets of calcium lactate were carried out using the paddle method of US Pharmacopeia using the following conditions.
- Paddle speed: 50 rpm
- Media: 0.1N HCl (0-120 min), phosphate buffer pH 6.8 (120-180 min)
- Temperature: 37° C.
- Analysis method: HPLC H) Results (1) Solubility of Calcium Lactate in Various Solvents The solubility of calcium lactate in isopropanol, ethanol, methanol and water is shown in Table 5. As can be seen from this table, the solubilities of pentahydrate form and dried form are different from each other. The pentahydrate form of calcium lactate showed a high solubility of 99.48 mg/mL in water as expected, but 0.024 mg/mL in isopropanol, 1.464 mg/mL in ethanol, and 507.17 mg/mL in methanol. (Even though the solubility of calcium lactate is very high in methanol, methanol cannot be used as a coating solvent in S. Korea since the case of Gincomin tablet.) The solution of dried calcium lactate in methanol is much higher than that of pentahydrate form. But, the solution became highly viscous (like gel) at the concentration of 750 mg/mL of dried calcium lactate in methanol, so we could not add any more drug to determine the solubility.

TABLE 5

Solubility of calcium lactate (pentahydrate and dried form) in various solvents at 30° C. (mean ± SD, n = 3)

| | Solubility, mg/mL | |
| --- | --- | --- |
| Solvent | calcium lactate pentahydrate (29.19% water) | dried calcium lactate (4.05% water) |
| Isopropanol | 0.024 ± 0.003 | 0.046 ± 0.016 |
| | calcium lactate anhydrous: 0.017 | calcium lactate anhydrous: 0.044 |
| | Water: 0.007 | Water: 0.002 |
| Ethanol | 1.464 ± 0.02 | 1.206 ± 0.050 |
| | calcium lactate anhydrous: 1.036 | calcium lactate anhydrous: 1.157 |
| | Water: 0.427 | Water: 0.049 |
| Water | 99.48 ± 0.34 | 73.49 ± 1.064 |
| | calcium lactate anhydrous: 70.44 | calcium lactate anhydrous: 70.51 |
| | Water: 29.04 | Water: 2.98 |
| Methanol | 507.17 ± 8.74 | >750* |
| | calcium lactate anhydrous: 359.11 | |
| | Water: 148.05 | |

*The solution became highly viscous (like gel) at the concentration of 750 mg/mL of dried calcium lactate in methanol, so we could not add any more drug to determine the solubility.

(2) Dissolution of Drug from Enteric-Coated Tablets of Calcium Lactate

The tablets were enteric-coated using polyvinyl acetate phthalate as an enteric-coating agent at the level of 0%, 2.1%, 5.7%, 8.3%, and 10.9%. Dissolution tests of the tablets were carried out in 0.1N HCL at pH 6.8 for 120 minutes followed by another test after adjusting pH 6.8 with phosphate buffer for 1 hour. The results are shown in Table 6 and FIG. 3.

TABLE 6

Drug release from enteric-coated tablets containing calcium lactate (mean ± SD, n = 3)

| | Drug Released, % | | | | |
| --- | --- | --- | --- | --- | --- |
| Time (min) | EC 10.9% | EC 8.3% | EC 5.7% | EC 2.1% | uncoated |
| 0 | 0.0 ± 0.0 | 0.0 ± 0.0 | 0.0 ± 0.0 | 0.0 ± 0.0 | 0.0 ± 0.0 |
| 15 | 0.0 ± 0.0 | 0.0 ± 0.0 | 0.0 ± 0.0 | 0.0 ± 0.0 | 97.7 ± 3.5 |
| 30 | 0.0 ± 0.0 | 0.0 ± 0.0 | 0.0 ± 0.0 | 0.0 ± 0.0 | 97.8 ± 2.2 |
| 60 | 0.0 ± 0.0 | 0.0 ± 0.0 | 0.0 ± 0.0 | 6.9 ± 1.5 | 97.3 ± 2.7 |
| 90 | 0.0 ± 0.0 | 0.0 ± 0.0 | 0.0 ± 0.0 | 23.8 ± 11.1 | 97.2 ± 2.4 |
| 120 | 0.0 ± 0.0 | 0.0 ± 0.0 | 0.0 ± 0.0 | 41.2 ± 18.5 | 97.3 ± 3.0 |
| 130 | 0.0 ± 0.0 | 0.0 ± 0.0 | 8.3 ± 3.3 | 100.3 ± 1.4 | |
| 140 | 2.4 ± 4.1 | 54.9 ± 19.8 | 101.4 ± 0.4 | 101.1 ± 1.3 | |
| 150 | 96.4 ± 3.3 | 99.8 ± 0.9 | 101.5 ± 0.4 | 101.2 ± 0.9 | |
| 165 | 99.4 ± 1.7 | 100.1 ± 0.9 | 101.5 ± 0.4 | 101.0 ± 1.3 | |
| 180 | 99.1 ± 2.0 | 100.0 ± 0.8 | 101.7 ± 0.1 | 101.4 ± 1.0 | |

The dissolution test with the uncoated tablet in 0.1N HCl solution for 120 min showed that the drug had been completely dissolved at 15 minutes. In the case of 2.1% enteric-coated tablets, the dissolution of the drug started at 60 minutes in 0.1N HCl solution and about 41% of the drug has been dissolved at 120 minutes. After that, the drug was completely dissolved at 10 minutes in pH 6.8 phosphate buffer. It is considered that the enteric coating is not sufficient as the dissolution started in the acidic solution as described above.

On the other hand, in the case of tablets coated with 5.7% or more, no drug was dissolved from 0.1N HCl solution to 120 minutes. Afterwards, at pH 6.8, the drug was completely dissolved at 20 minutes from the 5.7% enteric-coated tablets, at 30 minutes from 8.3% enteric-coated tablets, and at 45 minutes from 10.9% enteric-coated tablets.

Figure 3:
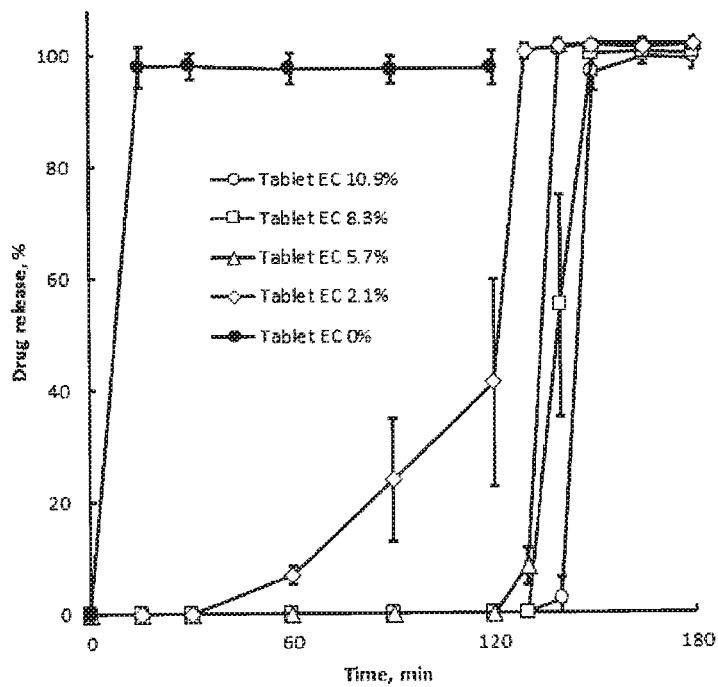
FIG. 3. Drug release profile from enteric-coated tablets containing calcium lactate (mean±SD, n=3).

Based on the results, as shown in FIG. 3, it was found that about 5% of enteric-coating for tablets showed sufficient acid resistance in stomach and can be completely dissolved in a short time.

(3) Dissolution of Drug from Enteric Pellet of Calcium Lactate

Figure 4:
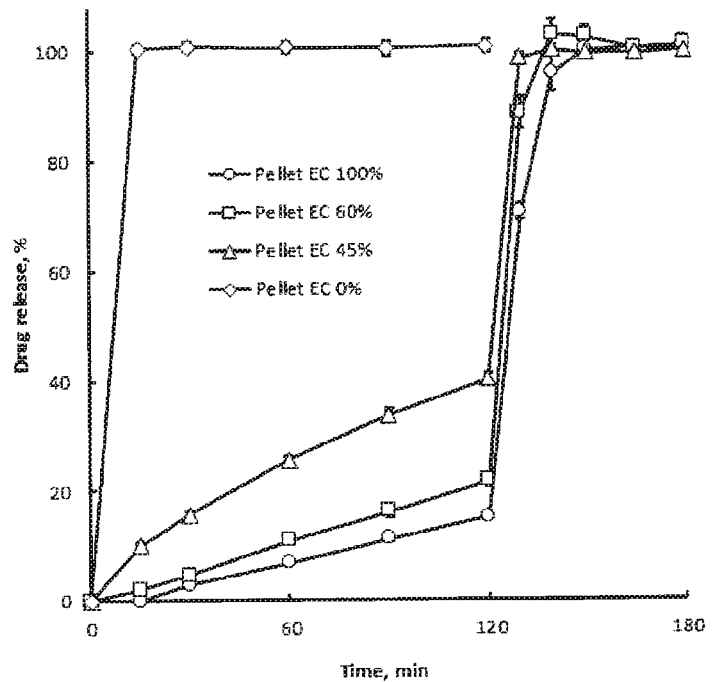
FIG. 4. Drug release profile from enteric-coated pellets containing calcium lactate (mean±SD, n=3)
Figure 5A:
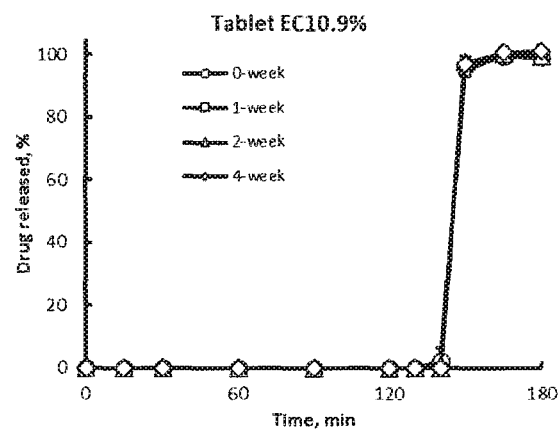
FIGS. 5A-5D. Drug release profiles of enteric-coated tablets of calcium lactate with different amount of enteric-coating materials after stored at 40° C. for 4 weeks (mean±SD, n=3) (A; 10.9%, B; 8.3%, C; 5.7%, D; 2.1%)
Figure 5B:
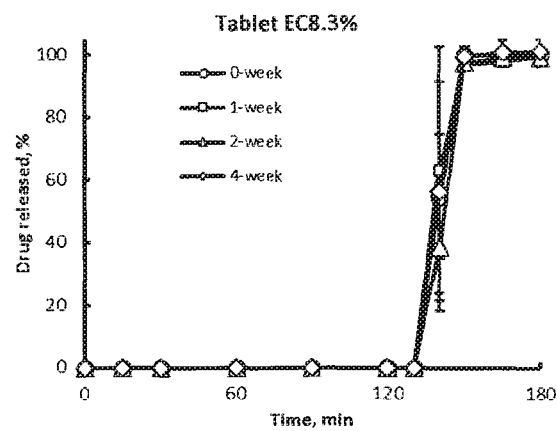
Figure 5C:
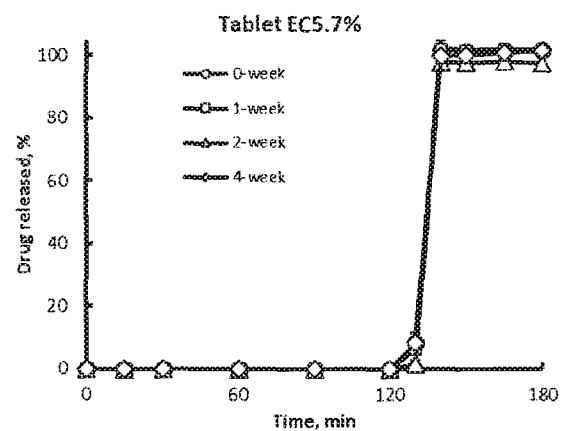
Figure 5D:
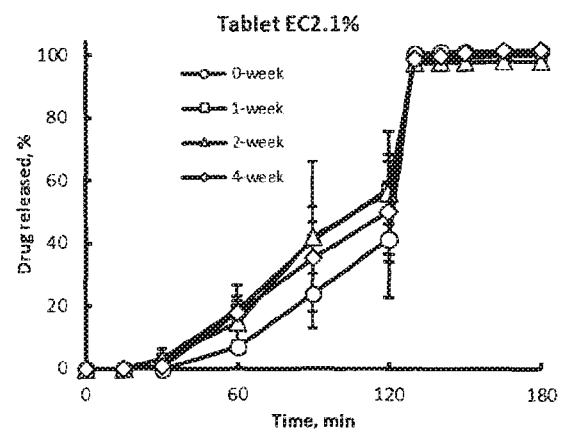
Figure 6A:
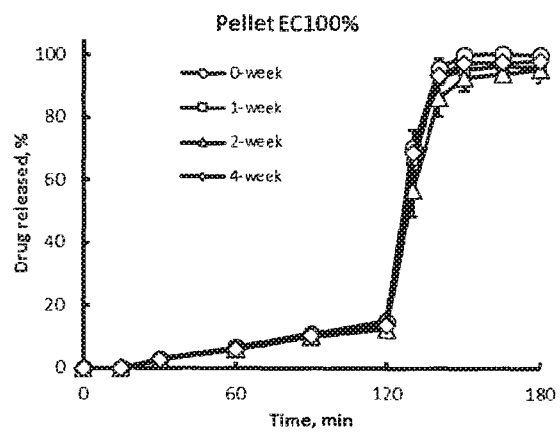
FIGS. 6A-6D. Drug release profiles of enteric-coated pellets of calcium lactate with different amount of enteric-coating materials after stored at 40° C. for 4 weeks (mean f SD, n=3) (A; 100%, B; 60%, C; 45%, D; uncoated)
Figure 6B:
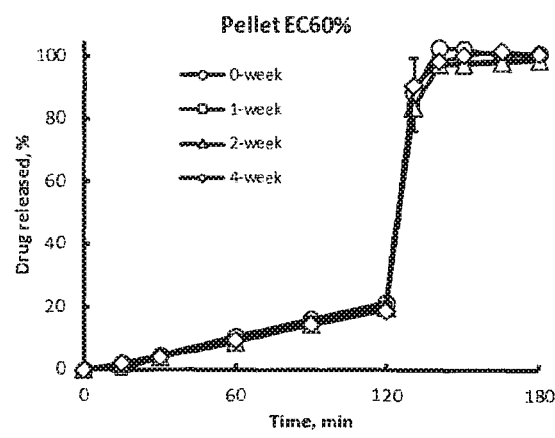
Figure 6C:
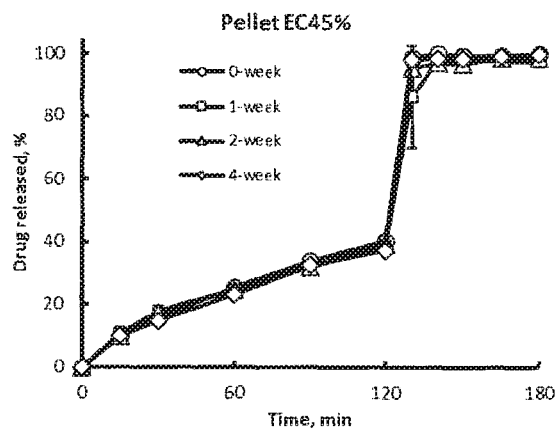
Figure 6D:
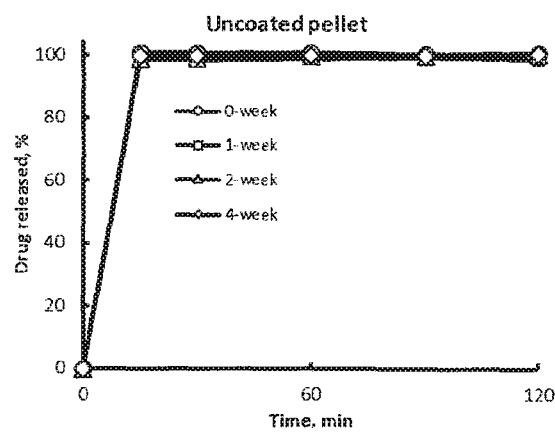

The pellets were enteric-coated using HPMCP as an enteric-coating agent at the level of 0%, 45%, 60%, and 100%. Dissolution tests of the pellets were carried out in 0.1N HCL for 120 minutes followed by another test after adjusting pH 6.8 with phosphate buffer for 1 hour. The results are shown in Table 7 and FIG. 4. As can be seen from these data, the drug was fully dissolved after 15 minutes of the test as in the case of the uncoated tablet.

TABLE 7

Drug release from enteric-coated pellets containing calcium lactate (mean ± SD, n = 3)

| Time (min) | Drug released, % | | | |
|---|---|---|---|---|
| | EC100% | EC 60% | EC 45% | uncoated |
| 0 | 0.0 ± 0.0 | 0.0 ± 0.0 | 0.0 ± 0.0 | 0.0 ± 0.0 |
| 15 | 0.0 ± 0.0 | 2.0 ± 0.0 | 10.0 ± 0.4 | 100.6 ± 0.8 |
| 30 | 2.9 ± 0.2 | 4.6 ± 0.4 | 15.6 ± 0.8 | 100.9 ± 0.8 |
| 60 | 6.8 ± 0.3 | 10.8 ± 0.3 | 25.5 ± 0.8 | 100.8 ± 1.1 |
| 90 | 11.1 ± 0.3 | 16.0 ± 0.9 | 33.8 ± 1.2 | 100.6 ± 1.2 |
| 120 | 15.1 ± 0.3 | 21.6 ± 0.9 | 40.3 ± 1.1 | 100.9 ± 1.2 |
| 130 | 70.7 ± 1.5 | 88.7 ± 2.9 | 98.7 ± 0.6 | |
| 140 | 95.7 ± 3.3 | 102.9 ± 2.7 | 100.1 ± 0.7 | |
| 150 | 100.1 ± 0.7 | 102.5 ± 2.0 | 99.5 ± 0.4 | |
| 165 | 100.4 ± 0.7 | 100.3 ± 0.7 | 99.6 ± 0.5 | |
| 180 | 100.3 ± 0.8 | 101.0 ± 1.8 | 100.1 ± 1.0 | |

For 45% enteric-coated pellets, the drug began to dissolve at 15 minutes in 0.1N HCl and about 40% of the drug was dissolved at 120 minutes.

This result was similar with enteric-coated pellets at the higher level. In 60% enteric-coated pellets, about 22% drug was dissolved, and in 100% enteric-coated pellets, about 15% drug was dissolved. It indicates that the enteric-coatings was not complete. Subsequently, the drug was completely dissolved at 140 minutes (20 minutes in the intestinal fluid) for the 45% and 60% enteric-coated pellets and at 150 minutes (30 minutes in the intestinal fluid) for the 100% enteric-coated pellets. The reason of this result may due to the inconsistent size of the raw material of calcium lactate used in the production and, thus, some fine granules were not coated or coated thinner than other fine granules. This extent of dissolution is not negligible but it can be controlled with 150% of enteric-coating at actual production and it is not considered large number for the production at pilot test.

(4) Stability Test of Enteric Coated Calcium Lactate

The stability of calcium lactate preparation was observed with enteric-coated tablets with polyvinyl acetate phthalate at the level of 2.1%, 5.7%, 8.3% and 10.9%, and pellets coated with HPMC at the level of 45%, 60%, and 100%. The stabilities of the enteric-coated tablets and pellets were evaluated with respect to dissolution profile after storage at 40° C. for 1, 2 and 4 weeks. The results are shown in Tables 8 and 9, and also the stabilities of calcium lactate at each enteric-coated level are presented in FIGS. 5 and 6, respectively.

As shown in Table 8 and FIG. 5, there was no difference in dissolution profile of enteric-coated tablets between at time and after storage for 4 weeks at 40° C., except in the case of 2.1% enteric-coated tablets. However, this difference is considered due to the uneven coating of the small amount of coating rather than the effect of storage temperature. There were no differences in the dissolution profiles among the samples stored for 1, 2, and 4 weeks. Overall, there is no change in the dissolution profile of enteric coating tablets containing calcium lactate as the main ingredient when stored for 4 weeks.

Also, as shown in Table 9 and FIG. 6, there was no difference in dissolution profile of enteric-coated pellets between at 0 time and after storage for 4 weeks at 40° C. Overall, enteric-coated calcium lactate preparations were stable and their dissolution profiles were not changed even when stored at high temperatures.

(I) Conclusions

In order to protect calcium lactate, which is susceptible to gastric acid and intestinal enzymes, from the stomach and to improve its absorption in the small intestine before it reaches the large intestine, calcium lactate was formulated into enteric-coated tablets and capsules. Both preparations reached the goal of the research based on pharmaceutical evaluation. It was concluded that tablet form is preferable when considering the easiness of manufacturing on the premise that the dosage to a human body of calcium lactate will be several tens of mg.

In addition, stabilities at 1, 2 and 4 weeks were measured at 40° C., an accelerated condition, and no difference was observed among the stabilities measured immediately before the test.

However, in the case of tablets coated with a content of 2.1%, there was a slight difference in the dissolution profile between the profiles measured at 0 time, but no significant difference of the stabilities among the samples.

TABLE 8

Drug release from enteric-coated tablets containing calcium lactate stored at 40° C. for 1, 2 and 4 weeks (mean ± SD, n = 3)

| | Time | Drug released, % | | | | |
|---|---|---|---|---|---|---|
| Week | (min) | EC 10.9% | EC 8.3% | EC 5.7% | EC 2.1% | uncoated |
| 1 | 0 | 0.0 ± 0.0 | 0.0 ± 0.0 | 0.0 ± 0.0 | 0.0 ± 0.0 | 0.0 ± 0.0 |
| | 15 | 0.0 ± 0.0 | 0.0 ± 0.0 | 0.0 ± 0.0 | 0.0 ± 0.0 | 98.1 ± 1.1 |

TABLE 8-continued

Drug release from enteric-coated tablets containing calcium lactate stored at 40° C. for 1, 2 and 4 weeks (mean ± SD, n = 3)

| Week | Time (min) | EC 10.9% | EC 8.3% | EC 5.7% | EC 2.1% | uncoated |
|---|---|---|---|---|---|---|
| | 30 | 0.0 ± 0.0 | 0.0 ± 0.0 | 0.0 ± 0.0 | 3.3 ± 1.5 | 98.4 ± 1.8 |
| | 60 | 0.0 ± 0.0 | 0.0 ± 0.0 | 0.0 ± 0.0 | 18.9 ± 4.1 | 98.6 ± 1.0 |
| | 90 | 0.0 ± 0.0 | 0.0 ± 0.0 | 0.0 ± 0.0 | 41.0 ± 10.5 | 98.3 ± 1.3 |
| | 120 | 0.0 ± 0.0 | 0.0 ± 0.0 | 6.2 ± 3.4 | 98.6 ± 1.4 | 98.6 ± 1.3 |
| | 130 | 0.0 ± 0.0 | 0.0 ± 0.0 | 8.3 ± 3.3 | 100.3 ± 1.4 | |
| | 140 | 0.0 ± 0.0 | 63.3 ± 39.4 | 102.2 ± 2.7 | 99.1 ± 1.2 | |
| | 150 | 95.2 ± 3.8 | 96.9 ± 1.0 | 101.9 ± 1.6 | 99.5 ± 1.3 | |
| | 165 | 99.9 ± 0.8 | 97.9 ± 1.7 | 101.8 ± 1.8 | 99.7 ± 1.2 | |
| | 180 | 100.1 ± 1.5 | 99.4 ± 1.8 | 101.9 ± 1.6 | 100.0 ± 1.5 | |
| 2 | 0 | 0.0 ± 0.0 | 0.0 ± 0.0 | 0.0 ± 0.0 | 0.0 ± 0.0 | 0.0 ± 0.0 |
| | 15 | 0.0 ± 0.0 | 0.0 ± 0.0 | 0.0 ± 0.0 | 0.0 ± 0.0 | 97.8 ± 1.7 |
| | 30 | 0.0 ± 0.0 | 0.0 ± 0.0 | 0.0 ± 0.0 | 3.2 ± 3.2 | 98.2 ± 2.1 |
| | 60 | 0.0 ± 0.0 | 0.0 ± 0.0 | 0.0 ± 0.0 | 14.8 ± 6.9 | 97.8 ± 1.5 |
| | 90 | 0.0 ± 0.0 | 0.0 ± 0.0 | 0.0 ± 0.0 | 42.0 ± 23.8 | 98.5 ± 1.4 |
| | 120 | 0.0 ± 0.0 | 0.0 ± 0.0 | 0.0 ± 0.0 | 56.1 ± 19.5 | 98.6 ± 1.6 |
| | 130 | 0.0 ± 0.0 | 0.0 ± 0.0 | 1.7 ± 3.0 | 97.5 ± 0.5 | |
| | 140 | 0.0 ± 0.0 | 38.7 ± 20.3 | 97.7 ± 2.2 | 97.8 ± 0.8 | |
| | 150 | 97.7 ± 0.9 | 97.5 ± 2.4 | 97.9 ± 1.8 | 97.7 ± 0.4 | |
| | 165 | 100.1 ± 2.0 | 99.0 ± 1.9 | 98.1 ± 2.0 | 98.0 ± 0.4 | |
| | 180 | 99.6 ± 1.1 | 99.1 ± 2.8 | 97.6 ± 1.7 | 98.1 ± 0.4 | |
| 4 | 0 | 0.0 ± 0.0 | 0.0 ± 0.0 | 0.0 ± 0.0 | 0.0 ± 0.0 | 0.0 ± 0.0 |
| | 15 | 0.0 ± 0.0 | 0.0 ± 0.0 | 0.0 ± 0.0 | 0.0 ± 0.0 | 97.3 ± 0.8 |
| | 30 | 0.0 ± 0.0 | 0.0 ± 0.0 | 0.0 ± 0.0 | 1.1 ± 1.8 | 97.6 ± 1.0 |
| | 60 | 0.0 ± 0.0 | 0.0 ± 0.0 | 0.0 ± 0.0 | 17.7 ± 9.0 | 97.6 ± 0.9 |
| | 90 | 0.0 ± 0.0 | 0.0 ± 0.0 | 0.0 ± 0.0 | 35.4 ± 11.3 | 97.8 ± 0.3 |
| | 120 | 0.0 ± 0.0 | 0.0 ± 0.0 | 0.0 ± 0.0 | 50.1 ± 16.0 | 98.3 ± 0.6 |
| | 130 | 0.0 ± 0.0 | 0.0 ± 0.0 | 8.4 ± 1.1 | 98.9 ± 1.0 | |
| | 140 | 0.0 ± 0.0 | 56.6 ± 34.9 | 99.8 ± 0.6 | 99.8 ± 1.0 | |
| | 150 | 97.1 ± 2.5 | 99.4 ± 3.1 | 100.3 ± 0.6 | 100.9 ± 0.8 | |
| | 165 | 100.6 ± 2.0 | 100.7 ± 3.8 | 100.9 ± 0.8 | 101.4 ± 0.8 | |
| | 180 | 101.1 ± 2.0 | 101.2 ± 3.8 | 101.4 ± 0.8 | 101.9 ± 1.0 | |

TABLE 9

Drug release from enteric-coated pellets containing calcium lactate stored at 40° C. for 1, 2 and 4 weeks (mean ± SD, n = 3)

| Week | Time (min) | EC 100% | EC 60% | EC 45% | uncoated |
|---|---|---|---|---|---|
| 1 | 0 | 0.0 ± 0.0 | 0.0 ± 0.0 | 0.0 ± 0.0 | 0.0 ± 0.0 |
| | 15 | 0.0 ± 0.0 | 2.0 ± 0.0 | 10.8 ± 1.7 | 98.4 ± 0.3 |
| | 30 | 2.7 ± 0.2 | 4.0 ± 0.3 | 17.9 ± 0.8 | 98.4 ± 0.3 |
| | 60 | 6.1 ± 0.5 | 9.3 ± 0.1 | 25.0 ± 1.4 | 98.9 ± 0.3 |
| | 90 | 10.0 ± 0.7 | 15.1 ± 0.4 | 32.3 ± 1.3 | 99.1 ± 0.4 |
| | 120 | 13.7 ± 1.0 | 20.0 ± 0.5 | 39.0 ± 2.5 | 98.9 ± 0.4 |
| | 130 | 66.3 ± 5.8 | 84.1 ± 1.3 | 86.3 ± 16.4 | |
| | 140 | 93.2 ± 6.4 | 97.2 ± 1.8 | 98.3 ± 3.7 | |
| | 150 | 95.6 ± 4.5 | 98.5 ± 1.2 | 98.2 ± 3.2 | |
| | 165 | 96.3 ± 1.8 | 98.9 ± 1.2 | 97.8 ± 0.6 | |
| | 180 | 96.1 ± 3.9 | 99.8 ± 1.6 | 97.3 ± 1.4 | |
| 2 | 0 | 0.0 ± 0.0 | 0.0 ± 0.0 | 0.0 ± 0.0 | 0.0 ± 0.0 |
| | 15 | 0.0 ± 0.0 | 2.0 ± 0.1 | 9.6 ± 1.3 | 98.9 ± 1.6 |
| | 30 | 2.7 ± 0.4 | 3.8 ± 0.3 | 17.3 ± 0.8 | 99.2 ± 1.4 |
| | 60 | 6.1 ± 0.2 | 8.8 ± 0.2 | 24.3 ± 1.8 | 99.8 ± 1.1 |
| | 90 | 9.9 ± 0.3 | 14.3 ± 0.5 | 31.9 ± 1.5 | 99.9 ± 1.3 |
| | 120 | 12.5 ± 0.9 | 19.7 ± 0.2 | 39.2 ± 0.5 | 100.3 ± 1.4 |
| | 130 | 56.7 ± 8.2 | 83.7 ± 7.7 | 95.4 ± 0.6 | |
| | 140 | 86.4 ± 5.9 | 97.3 ± 1.6 | 97.1 ± 0.3 | |
| | 150 | 92.6 ± 4.0 | 97.3 ± 1.0 | 96.9 ± 1.0 | |
| | 165 | 94.2 ± 1.3 | 98.2 ± 1.5 | 98.8 ± 2.3 | |
| | 180 | 95.4 ± 4.2 | 98.6 ± 1.4 | 98.7 ± 2.3 | |
| 4 | 0 | 0.0 ± 0.0 | 0.0 ± 0.0 | 0.0 ± 0.0 | 0.0 ± 0.0 |
| | 15 | 0.0 ± 0.0 | 2.1 ± 0.5 | 10.1 ± 0.8 | 99.7 ± 0.2 |
| | 30 | 2.6 ± 0.5 | 4.1 ± 0.3 | 14.7 ± 0.9 | 99.9 ± 0.6 |
| | 60 | 6.1 ± 1.0 | 9.3 ± 0.2 | 23.3 ± 0.8 | 99.6 ± 0.2 |
| | 90 | 10.3 ± 1.5 | 14.5 ± 0.2 | 32.6 ± 0.5 | 99.7 ± 0.3 |
| | 120 | 13.6 ± 1.7 | 18.9 ± 0.4 | 37.2 ± 0.5 | 100.4 ± 0.3 |
| | 130 | 69.0 ± 7.0 | 90.8 ± 8.7 | 98.1 ± 1.2 | |
| | 140 | 93.4 ± 2.4 | 98.3 ± 1.3 | 98.3 ± 1.7 | |
| | 150 | 97.5 ± 1.2 | 100.4 ± 0.8 | 98.5 ± 1.4 | |
| | 165 | 97.7 ± 0.7 | 101.9 ± 0.4 | 99.2 ± 0.5 | |
| | 180 | 98.2 ± 1.5 | 100.9 ± 0.9 | 99.7 ± 0.7 | |

Example 11: Preparation of Capsules

1. Calcium lactate solution is sprayed on a seed, of a constant size using a fluid-bed granulator to form a drug layer, and the formed spherical granules are enteric coated.

2. Calcium lactate is sieved and selected only for a certain size, and it is enteric-coated using a fluid-bed granulator.

3. Calcium lactate is mixed with a binding agent dissolved in an organic solvent to produce a wet mass. It is granulated using an extruder and then spheronized using spheronizer to prepare spherical granules, which is then enteric-coated.

In preparing the spherical granules as described above, various pharmaceutically acceptable additives can be added as needed.

Although the spherical granulator was used, other types of granulators having similar functions in addition to the fluid-bed granulator can be used.

Examples of enteric-coating agents include hydroxypropyl methyl cellulose phthalate (HPMCP), cellulose acetate phthalate (CAP), polyvinyl acetate phthalate (PVAP), shellac, polymers of methacrylic acid and their esters (Eudratgit®). However, the present invention is not limited thereto, and includes a substance which can be used for enteric-coatings pharmaceuticals. As described above, the content of the capsules containing calcium lactate is enteric-coated by conventional methods using conventional additives and put into capsules of appropriate size to prepare capsules.

Alternatively, the capsule contents containing calcium lactate can be prepared using conventional additives by conventional methods, and the contents are put into capsules of appropriate sizes and the capsules are enteric-coated.

Example 12: Preparation of Tablets

Tablets containing calcium lactate are prepared using conventional additives by conventional methods and enteric-coated.

Alternatively, calcium lactate powder is enteric-coated and used to prepare the tablets using conventional additives in a conventional manner.

Furthermore, tablets containing calcium lactate are prepared by conventional methods using conventional additives and enteric-coated, and can be optionally sugar-coated using conventional additives by conventional methods.

Preparation Example 12-1

300 g of calcium lactate is milled using a hammer of Fitzmill at rotating speed of 500 rpm, and a fine powder passed through a 60 mesh sieve for production. This powder is added to 750 g of anhydrous ethanol to make a suspension. To this solution, 9.5 g of HPMC 2910 5 cps and 0.5 g of PEG are added under stirring and allowed to stand overnight. Using a fluid-bed coater, the solution is sprayed to 300 g of 20-25 seed at a temperature of about 40° C. to prepare a drug layer. The enteric-coating solution, HPMCP 95 and glycerin 5 dissolved in a mixture of ethanol:water (95:5), is sprayed on the granules so as to increase the weight of content by 30% of the core. (Alternatively, povidone (PVP K30) 150 g is added to the solution while stirring to dissolve completely.)

Preparation Example 12-2

300 g of calcium lactate is screened on a 60-mesh sieve and the fine granules remaining on the sieve are used for the preparation. The enteric-coating solution, HPMCP 95 and glycerin 5 dissolved in a mixture of ethanol:water (95:5), is sprayed on the granules so as to increase the weight of content by 150% of the core.

Production Example 12-3

First, calcium lactate (100 mg) and VIVAPUR 12 (49.25 mg, JRS Pharma, Rosenberg, Germany) are weighed and mixed well. Then, magnesium stearate (0.75 mg) is mixed with this mixture. This final mixture is compressed to 150 mg per tablet using 8 mm concave punch. The hardness is adjusted to 80-100 N. An enteric-coating solution is prepared by dissolving polyvinyl acetate phthalate in a mixture of isopropyl alcohol:methylene chloride (6:4) to contain 6% coating base. The solution is sprayed to the tablet to increase the weight of the tablet by 5%.

Example 13: In Vivo Efficacy of Long-Acting Formulation

Long-acting formulation was prepared by a weight ratio of: calcium lactate:polysaccharide (MC): oil (corn oil+ glyceryl monostearate)=1:4:10. The prepared composition formed a homogeneous solution phase which is easy to administer the injection to the patients. With this composition, the calcium lactate is continuously released for up to 15 days.

Tumorigenesis

Human colorectal cancer cells ($5 \times 10^6$) were transplanted to the flank of Balb/c nude mice. The size of the tumor was grown to 150-200 mm³ before calcium lactate administration.

Calcium Lactate Administration

Group 1: Vehicle administration (Control group).
Group 2: Calcium lactate (2 mg/kg) was subcutaneously administered twice a day (B.I.D) for 21 days.
Group 3: Long-acting formulation drug including calcium lactate (200 mg/kg) was subcutaneously administered once on the first day of experiment.
Group 4: Long-acting formulation drug including calcium lactate (400 mg/kg) was subcutaneously administered once on the first day of experiment.

Antitumor Efficacy

Tumor volume was measured 3 times per week until the end of experiment and was recorded by calculating minimum (M) and maximum (L) linear size of the tumors ($L \times M^2/2$). Tumor weight was measured after autopsy on the final day of experiment. Tumor mass was sectioned to 5 μm and then stained with hematoxylin and eosin for histological analysis.

Toxicity

The body weight of each animal was measured three times per week until the final day of experiment. After tumor biopsy, condition of the internal organs was observed.

Results

Figure 7:
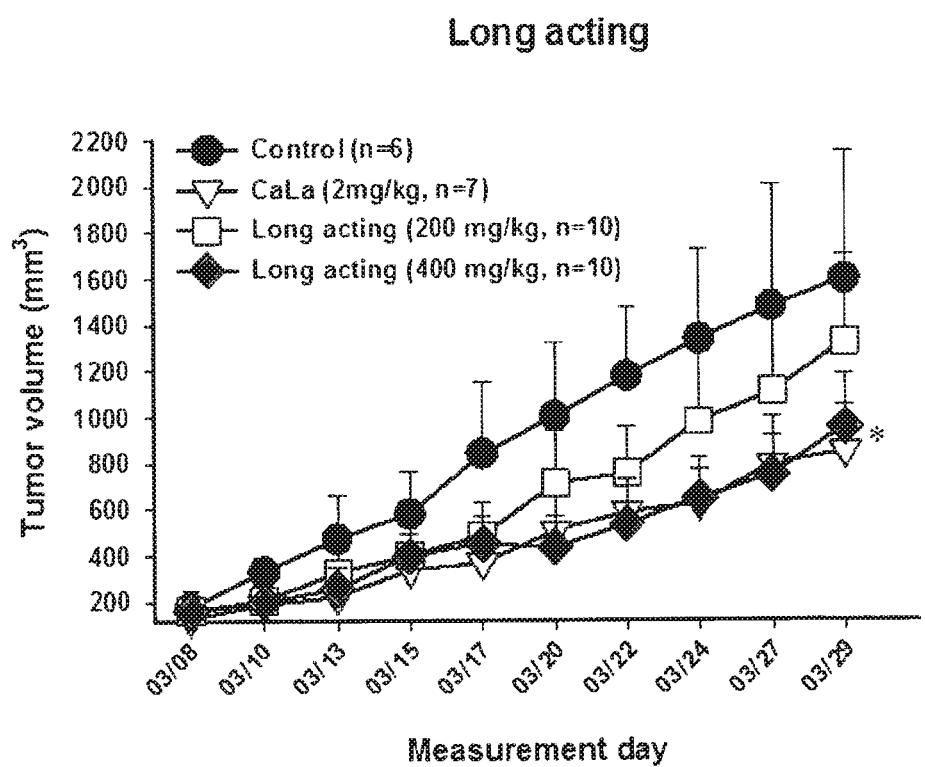
FIG. 7. Measurement of tumor volume following administration of long-acting formulations.

As shown in FIG. 7 (measurement of tumor volume), 2 weeks after a single administration of 200 mg/kg of long-acting formulation, the tumor growth was suppressed by about 20% as compared to the control group. The tumor growth was significantly suppressed by about 45% in the 400 mg/kg of long-acting-treated group as compared to the control group. The result for administration of 400 mg/kg of long-acting indicated a similar anticancer efficacy to that of daily calcium lactate administration for 21 days. These results indicated that long-acting formulations containing calcium lactate at the proper concentration can show the long-lasting antitumor efficacy similar to 3-week dosing of calcium lactate even with only one administration.

Figure 8:
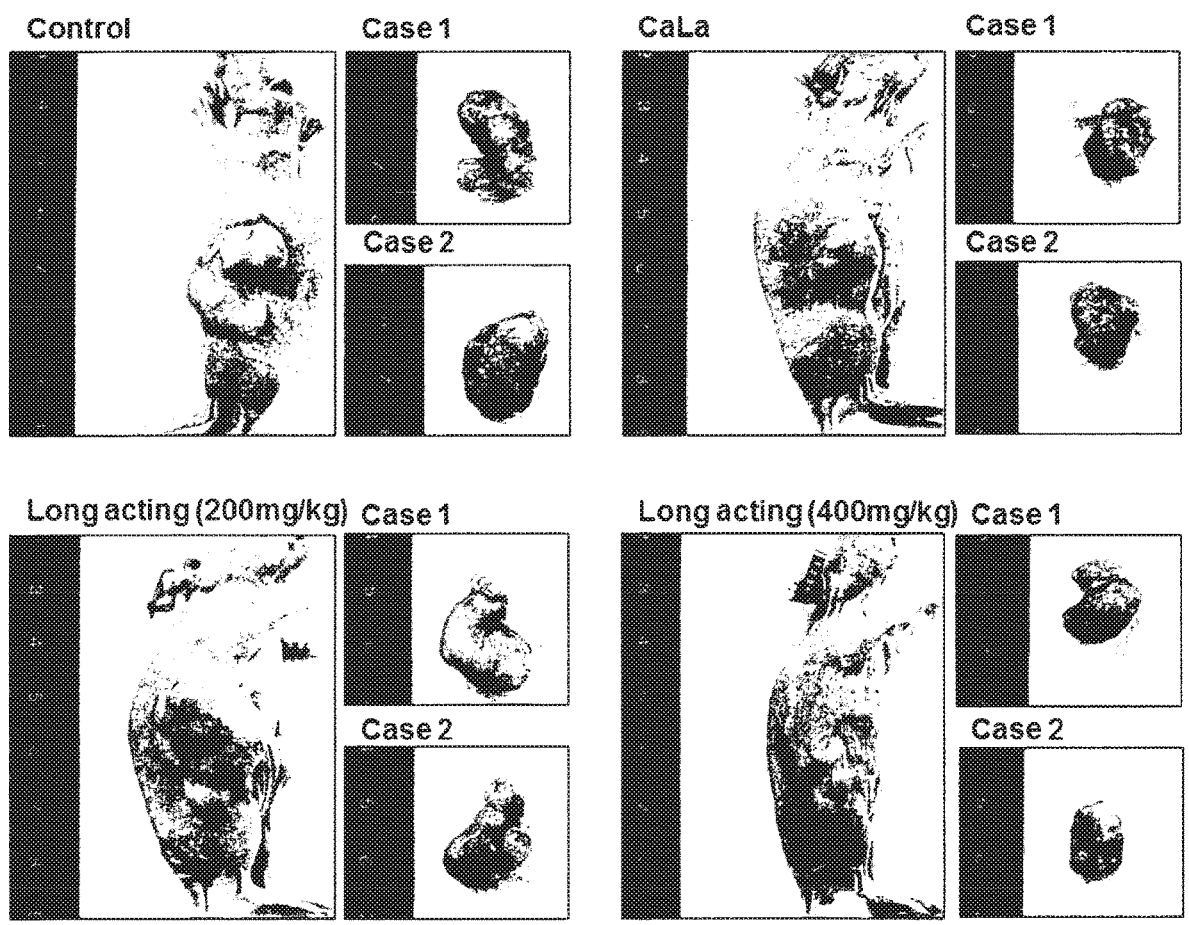
FIG. 8. The tumor size of calcium lactate- and long-acting (200 mg/kg and 400 mg/kg)-treated mice.

As shown in FIG. 8 (comparison of tumor growth), the tumor size of the group for 21 days calcium lactate- and the long-acting (400 mg/kg)-treated was clearly smaller than the control group. Although 200 mg/kg long-acting group showed similar tumor growth to the control group, inflammatory response by the calcium lactate was evidently observed in the tissue.

Figure 9:
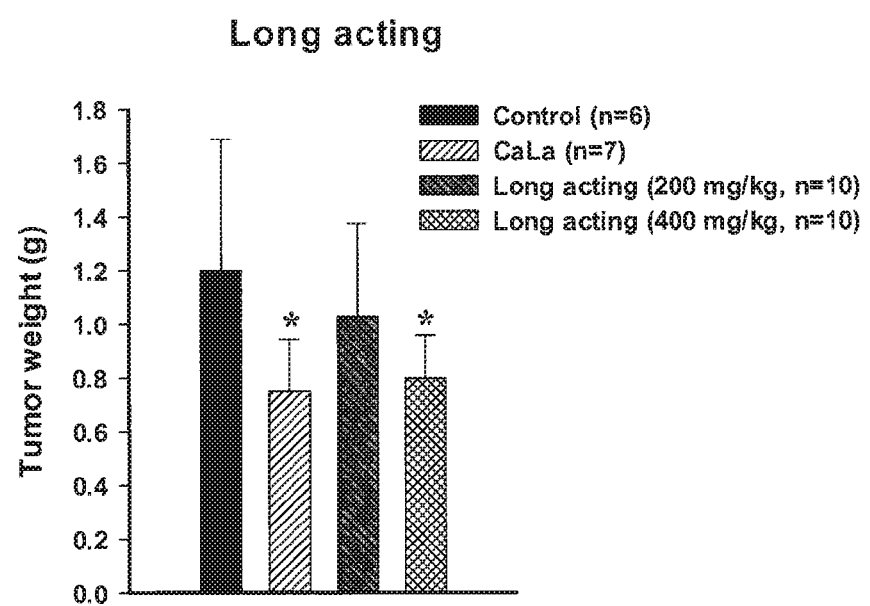
FIG. 9. Comparison of tumor weight following administration of long-acting formulations.

As shown in FIG. 9 (comparison of tumor weight), the average of the autopsied tumor weight at the end of the experiment is decreased by about 15% in the 200 mg/kg of long-acting-treated group as compared to the control group. And, the tumor weight was significantly decreased by about 40% in the 400 mg/kg of long-acting-treated group as compared to the control group, which result was similar to the daily treated group with calcium lactate for 21 days. These results indicated that long-acting formulations containing calcium lactate at the proper concentration can show the long-lasting antitumor efficacy similar to 3-week dosing of calcium lactate even with only one administration.

Figure 10:
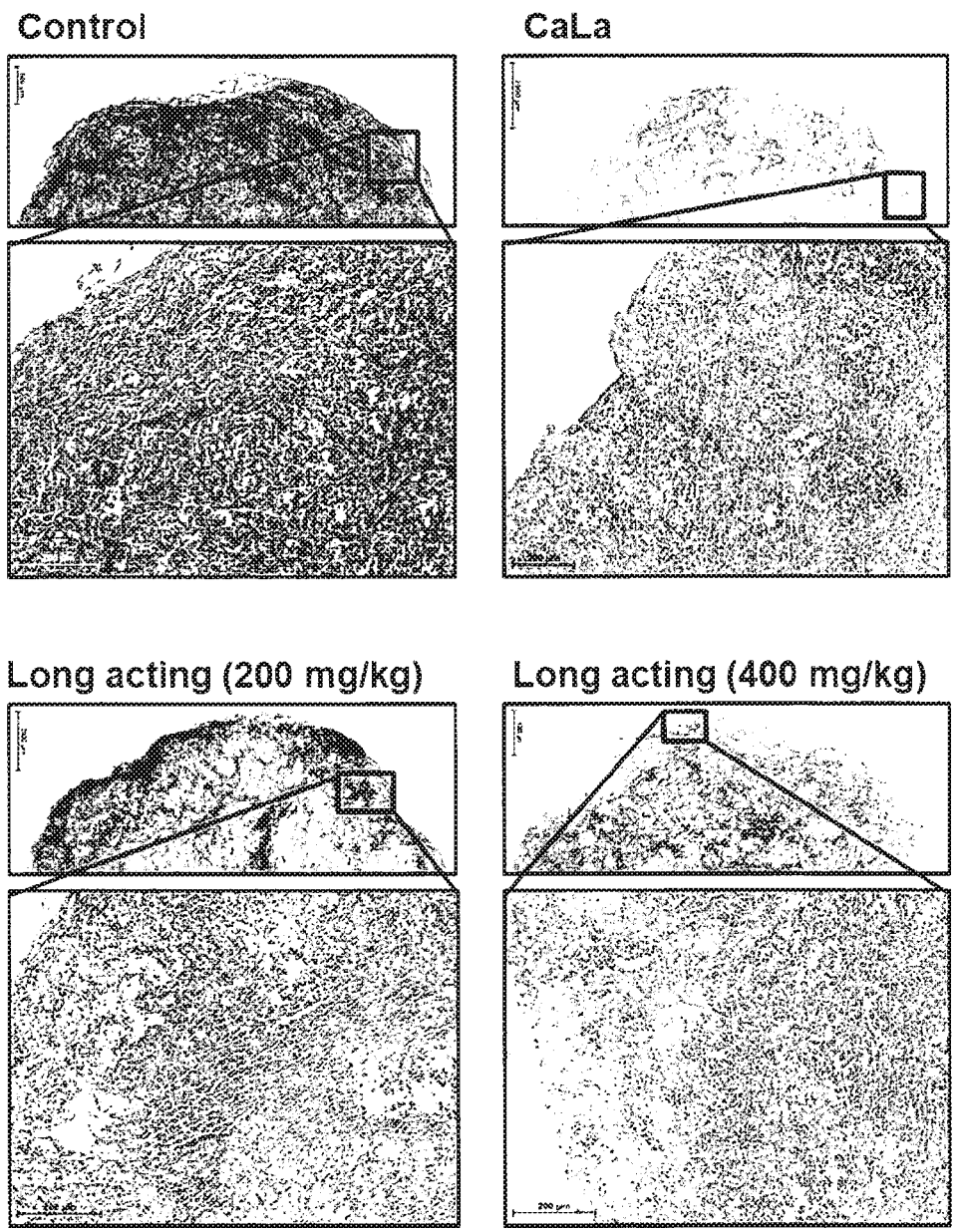
FIG. 10. Histological analysis for anticancer efficacy of long-acting formulations.

As shown in FIG. 10 (histological analysis), the group for long-acting formulation was able to confirm the internal necrosis in the tissues, such as daily administration with calcium lactate for 21 days, even though it was administered only once.

The body weight was measured three times per week, and there was no difference in body weight among the groups. This result indicated that long-acting formulation drugs gave no toxicity during the experiment.

An autopsy was carried out to check the functional status of the internal organs. It was confirmed that there was no effect on the internal organ including lung, heart, liver, and intestines even by long-acting formulation drugs.

Example 14: Rationale for Determining an Optimal Composition of Long Acting Formulation The long acting formulation was prepared by varying the composition, and then the solution state of the formulation, the possibility of injecting to the patients and the drug release characteristics were investigated.

TABLE 10

Characteristics of drug release by various composition weight ratios.

| Calcium lactate ratio | Polysaccharides (Methylcellulose or Pectin) ratio | Oil (Corn oil) + Polymer (Poloxamer) ratio | Formulation status | Parenteral injection | Drug release |
|---|---|---|---|---|---|
| 1 | <0.2 | 5-30 | Homogenous solution | Injectable | Rapid release |
| 1 | 0.2-5 | 5-30 | Homogenous solution | Injectable | Sustained release |
| 1 | >5 | 5-30 | Highly viscous or precipitates | Not injectable | |
| 1 | 0.2-5 | <5 | Highly viscous or precipitates | Not injectable | |
| 1 | 0.2-5 | >30 | Homogenous solution | Injectable but too much volume for subcutaneous injection | Sustained release |

A solution having a composition ratio of calcium lactate:polysaccharide:oil (corn oil)+polymer(poloxamer) (1:0.2:5~1:5:30) showed a homogeneous phase, which was injectable to the patient, and the drug was consistently released until 144 hours.

When the composition ratio of polysaccharide to calcium lactate was smaller than 0.2, the drug released rapidly within 6 to 24 hours.

When the composition of polysaccharide was 5 folds larger than calcium lactate, the solution was not injectable to the patients, because it was precipitated and highly viscous.

When the composition of oil (corn oil)+polymer (poloxamer) was 30 folds larger than calcium lactate, the solution was injectable, however the volume is too large to be suitable for subcutaneous injection.

Example 15: In Vivo Metastatic Effects

Cell Culture and Reagents

Human colorectal cancer cell line (HCT-116) was purchased from the American Type Culture Collection (Manassas, Va., USA). Cells were maintained in RPMI-1640 medium (Welgene, Daegu, South Korea) supplemented with 10% fetal bovine serum (Welgene, Daegu, South Korea), 100 IU/ml penicillin, and 100 µg/ml streptomycin (Welgene, Daegu, South Korea) in a humidified atmosphere of 5% $CO2$, at 37° C. Calcium lactate (CaLa) was purchased from Sigma-Aldrich (St Louis, Mo., USA). Calcium lactate was administered twice a day for 3 weeks via subcutaneous injection.

Intra-Splenic Injection

Mice were anesthetized with a 2% isoflurane. $5 \times 10^6$ of HCT116 cells were suspended in the 100 µL phosphate buffered saline for one injection. A small left abdominal flank incision was made and the spleen was exteriorized for the intra-splenic injection. The prepared cells were injected into the spleen with a 30-gauge needle. To prevent tumor cell leakage and bleeding, a cotton swab was held over the site of injection for 1 min. The injected spleen was returned to the abdomen and the wound was sutured with 6-0 black silk.

Results

Figure 11:
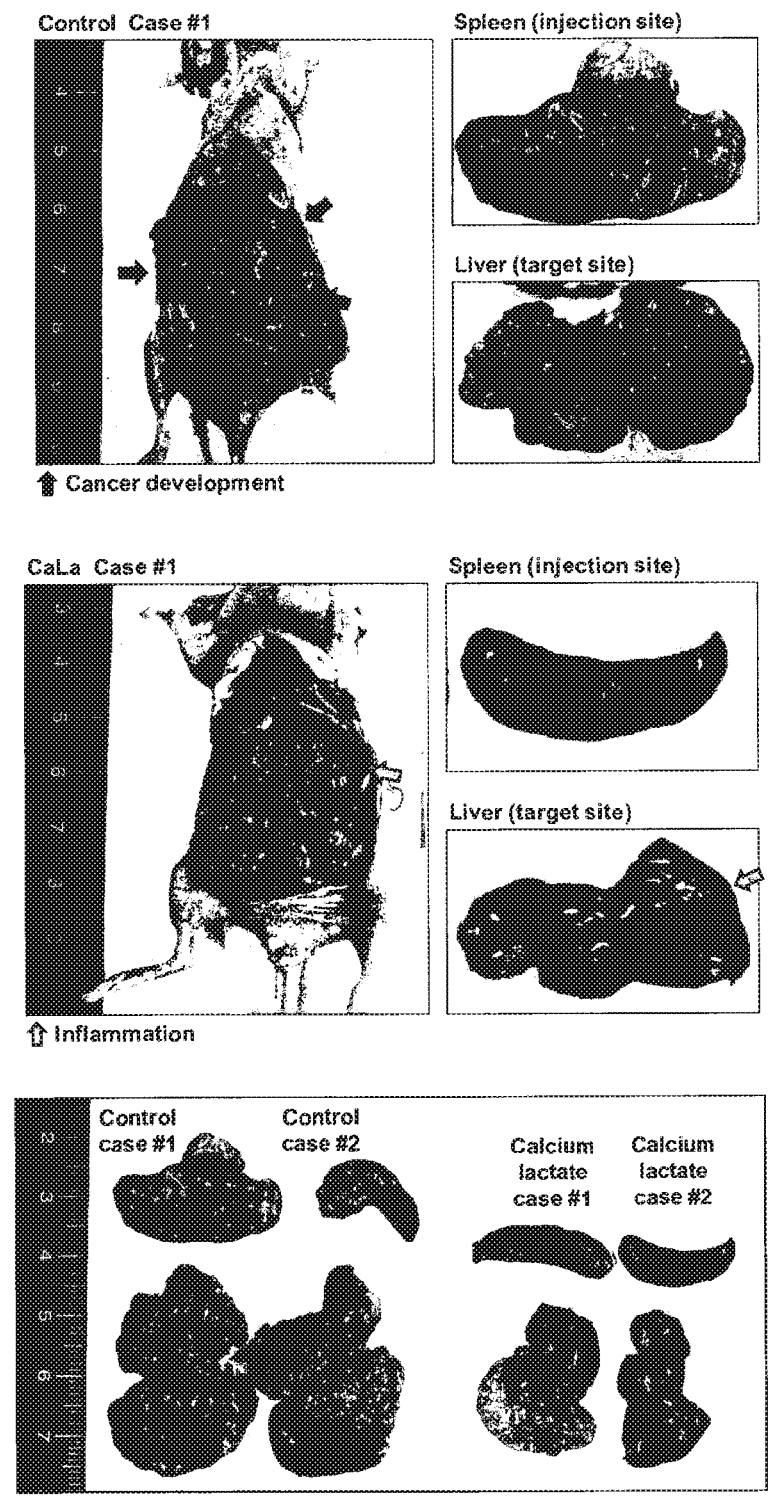
FIG. 11. Comparison of antitumor effect on liver metastasis after calcium lactate administration.

As shown in FIG. 11, metastasis was suppressed by calcium lactate administration as compared to the control, and even in the case tumor developed, it was confirmed that the inflammatory response was induced by the antitumor effect of the calcium lactate.

Example 16: In Vivo Efficacy of an Enteric Coating Formulation

Tumorigenesis

Human colorectal cancer cells ($2.5 \times 10^6$) were transplanted to the flank of Balb/c nude mice. The size of the tumor was grown to 150-200 mm³ before calcium lactate administration.

Figure 12:
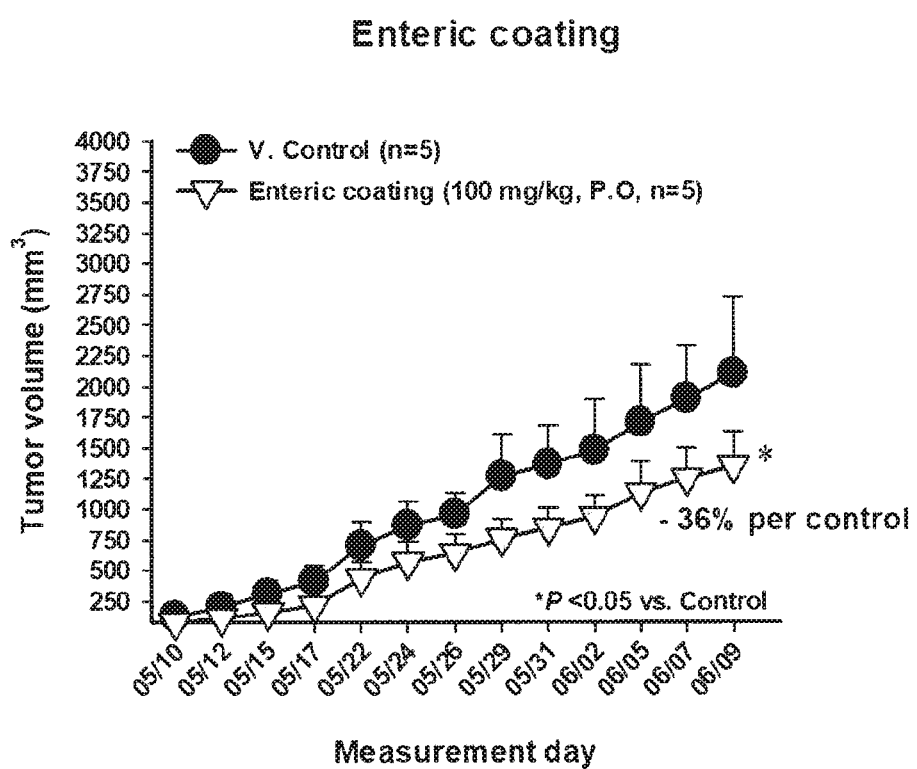
FIG. 12. Measurement of tumor volume following administration of an enteric coated formulation.
Figure 13:
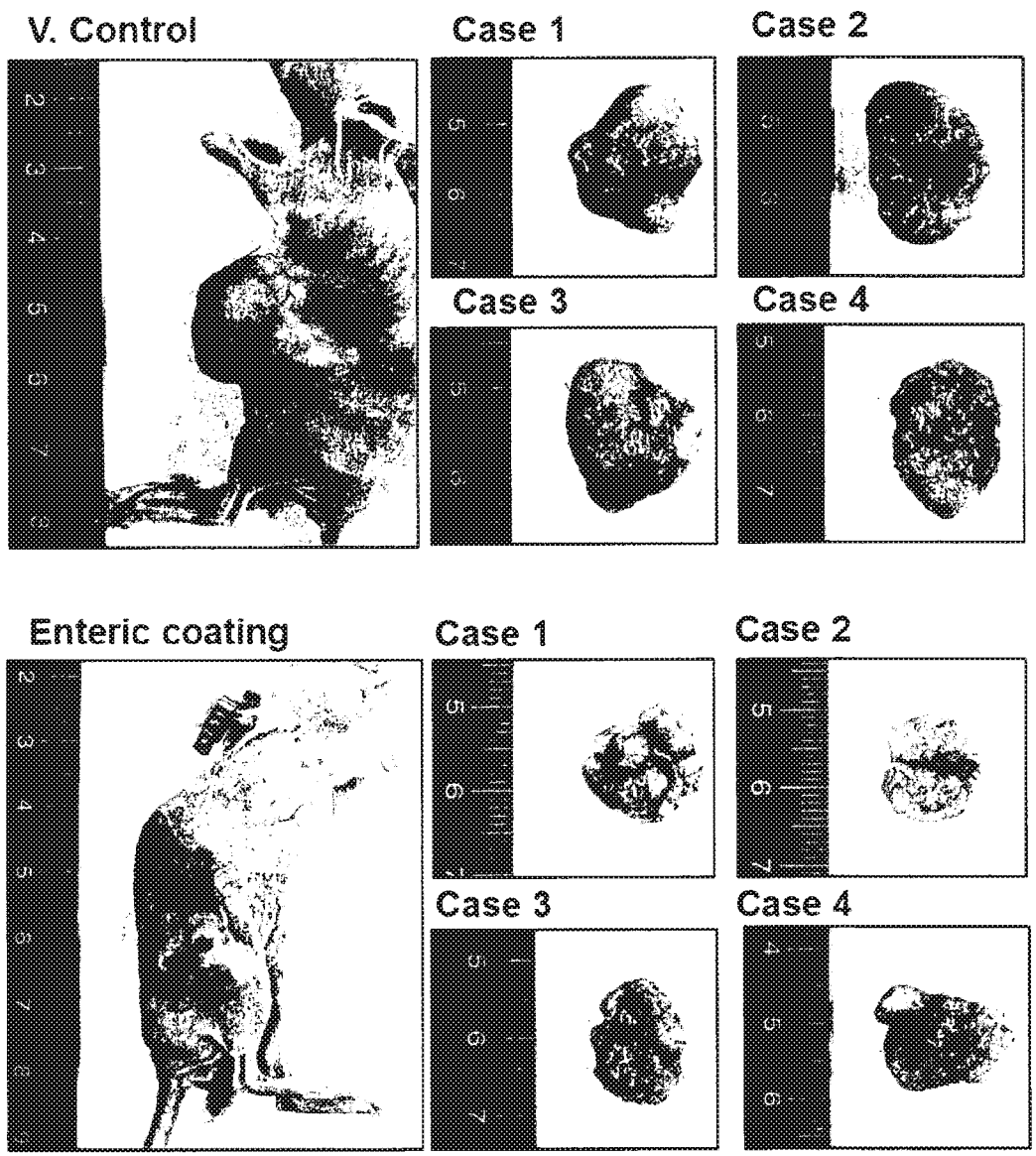
FIG. 13. Comparison of tumor growth following administration of an enteric coated formulation.
Figure 14:
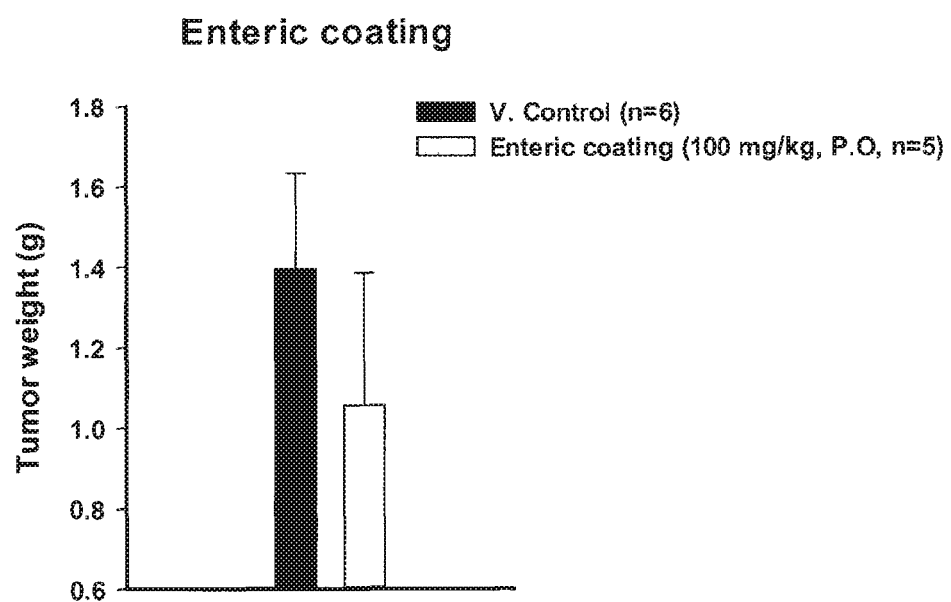
FIG. 14. Comparison of tumor weight following administration of an enteric coated formulation.

Calcium Lactate Administration
  Group 1: Vehicle administration (V. Control group).
  Group 2: Enteric coating formulation drug including calcium lactate (100 mg/kg) was orally administered 5 days per week for 3 weeks.
Antitumor Efficacy
  Tumor volume was measured 3 times per week until the end of experiment and was recorded by calculating minimum (M) and maximum (L) linear size of the tumors (L×M$^2$/2). Tumor weight was measured after autopsy on the final day of experiment.
Toxicity
  The body weight of each animal was measured three times per week until the final day of experiment. After tumor biopsy, condition of the internal organs was observed.
Results
  As shown in FIG. 12 (measurement of tumor volume), 3 weeks after a single administration of 100 mg/kg of enteric coating formulation, the tumor growth was suppressed by about 36% as compared to the control group.
  As shown in FIG. 13 (comparison of tumor growth), the tumor size of the group for the enteric coating (100 mg/kg)-treated was clearly smaller than the control group.
  As shown in FIG. 14 (comparison of tumor weight), the average of the autopsied tumor weight at the end of the experiment is decreased by about 25% in the 100 mg/kg of enteric coating-treated group as compared to the control group.
  The body weight was measured every week, and there was no difference in body weight between the groups. This result indicated that enteric coating formulation drugs gave no toxicity during the experiment.
  An autopsy was carried out to check the functional status of the internal organs. It was confirmed that there was no effect on the internal organ including lung, heart, liver, and intestines even by enteric coating formulation drugs.
  The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.
  The breadth and scope of the present invention should not be limited by any of the above-described exemplary embodiments, but should be defined only in accordance with the following claims and their equivalents.
  All of the various aspects, embodiments, and options described herein can be combined in any and all variations.
  All publications, patents, and patent applications mentioned in this specification are herein incorporated by reference to the same extent as if each individual publication, patent, or patent application was specifically and individually indicated to be incorporated by reference.

What is claimed is:

1. A method for treating colorectal cancer in a human subject in need thereof comprising:
  administering to the human subject an enteric coated oral composition, as a unit dose, comprising a therapeutically effective amount of calcium lactate, to a human subject in need thereof;
  wherein the oral composition comprising calcium lactate further comprises a polysaccharide, and is formulated for rapid disintegration in the intestinal environment, and the oral composition is coated with a pharmaceutically acceptable enteric coating; and
  wherein the therapeutically effective amount of calcium lactate in the unit dose ranges from 100 mg to 1000 mg,
  wherein the enteric coating comprises a hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof, and
  wherein the weight ratio of the calcium lactate and the enteric coating is from 10:0.5 to 1:1.5.

2. The method of claim 1, wherein the polysaccharide is microcrystalline cellulose.

3. The method of claim 1, further comprising administering a second anticancer agent or radiation.

4. The method of claim 3, wherein the second anticancer agent is Imatinib, 5-Fluorouracil, Irinotecan, Sunitinib, Oxaliplatin, Paclitaxel, Lapatinib, Trastuzumab, Gefitinib, Erlotinib, Methotrexate, Carboplatin, Docetaxel, Everolimus, Sorafenib, a carbonic anhydrase inhibitor, or a monocarboxylate transporter inhibitor.

5. The method of claim 3, wherein the calcium lactate and the second anticancer agent are administered simultaneously or sequentially.

6. The method of claim 3, wherein the radiation is provided to the subject in an amount of 2 Gy to 10 Gy per day.

7. The method of claim 1, wherein the oral composition is a unit dose in the form of a tablet, pellets or capsule.

8. The method of claim 7, wherein the enteric coating further comprises at least one pharmaceutically acceptable lubricant and at least one plasticizer.

9. A method for treating colorectal cancer in a human subject in need thereof comprising:
  administering to the human subject an enteric coated oral composition, as a unit dose, comprising a therapeutically effective amount of calcium lactate, to a human subject in need thereof;
  wherein the oral composition comprising calcium lactate further comprises a polysaccharide, and is formulated for rapid disintegration in the intestinal environment, and the oral composition is coated with a pharmaceutically acceptable enteric coating; and
  wherein the therapeutically effective amount of calcium lactate in the unit dose ranges from 100 mg to about 1000 mg,
  wherein the enteric coating comprises a hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof, and wherein the weight ratio of the calcium lactate and the enteric coating is from 10:0.5 to 1:1.5, and wherein a weight ratio of the calcium lactate and polysaccharide is from 1:0.1 to 1:5.

10. The method of claim 1, wherein the therapeutically effective amount of calcium lactate in the unit dose ranges from about 500 mg to about 750 mg.

11. The method of claim 1 wherein the polysachharide is a cellulose derivative.

12. The method of claim 11 wherein the cellulose derivative is carboxymethyl cellulose (CMC), ethyl cellulose (EC), and/or hydroxypropyl methyl cellulose (HPMC).

13. The method of claim 9, wherein the polysaccharide is a cellulose derivative.

14. the method of claim 13, wherein the cellulose derivative is carboxymethyl cellulose (CMC), ethyl cellulose (EC), and/or hydroxypropyl methyl cellulose (HPMC).

15. The method of claim 9, wherein the therapeutically effective amount of calcium lactate in the unit dose ranges from about 500 mg to about 750 mg.

16. The method of claim 9, further comprising administering a second anticancer agent or radiation.

17. The method of claim 16, wherein the second anticancer agent is lmatinib, 5-Fluorouracil, In notecan, Suniti nib, Oxaliplatin, Paclitaxel, Lapatini b, Trastuzumab, Gefitinib, Erlotinib, Methotrexate, Carboplatin, Docetaxel, Everolimus, Sorafenib, a carbonic anhydrase inhibitor, or a monocarboxylate transporter inhibitor.

18. The method of claim 16, wherein the radiation is provided to the subject in an amount of 2 Gy to 10 Gy per day.

19. The method of claim 9, wherein the oral composition is a unit dose in the form of a tablet, pellets or capsule.

* * * * *